(12) United States Patent
Lei et al.

(10) Patent No.: US 12,687,543 B2
(45) Date of Patent: Jul. 21, 2026

(54) TEST DEVICE FOR DETECTING ANALYTE IN LIQUID SAMPLE

(71) Applicant: Zhejiang Orient Gene Biotech Co., Ltd, Huzhou (CN)

(72) Inventors: Siyu Lei, Huzhou (CN); Jianqiu Fang, Huzhou (CN)

(73) Assignee: ZHEJIANG ORIENT GENE BIOTECH CO., LTD., Huzhou (CN)

( * ) Notice: Subject to any disclaimer, the term of this patent is extended or adjusted under 35 U.S.C. 154(b) by 602 days.

(21) Appl. No.: 18/301,598

(22) Filed: Apr. 17, 2023

(65) Prior Publication Data

US 2024/0345077 A1     Oct. 17, 2024

(51) Int. Cl.
*G01N 33/543*     (2006.01)
*G01N 33/76*      (2006.01)

(52) U.S. Cl.
CPC ....... *G01N 33/54388* (2021.08); *G01N 33/76* (2013.01)

(58) Field of Classification Search
CPC ..... Y02E 60/50; B01J 15/005; B01J 19/2485; B01J 2219/00135; B01J 2219/182; C01B 2203/0233; C01B 2203/0261; C01B 2203/0277; C01B 2203/0283; C01B 2203/044; C01B 2203/047; C01B 2203/066; C01B 2203/1023; C01B 2203/1041; C01B 2203/1047; C01B 2203/1082; C01B 2203/1094; C01B 2203/1205; C01B 2203/1223; C01B 2203/142; C01B 2203/1604; C01B 2203/1661; C01B 2203/82; C01B 3/16; C01B 3/26; C01B 3/323; C01B 3/38; C01B 3/583; H01M 8/0631; H01M 8/0662; F16B 35/06; G01N 33/54388; G01N 33/76; G01N 2333/59; H01J 37/32477; H01L 21/67069; H01L 21/6835; H01L 2924/3025; Y02P 20/52
See application file for complete search history.

(56) References Cited

U.S. PATENT DOCUMENTS

| | | | |
|---|---|---|---|
| 4,857,453 A | 8/1989 | Ullman et al. |
| 5,073,484 A | 12/1991 | Swanson et al. |
| 5,119,831 A | 6/1992 | Robin et al. |
| 5,185,127 A | 2/1993 | Vonk |
| 5,275,785 A | 1/1994 | May et al. |
| 5,352,410 A | 10/1994 | Hansen et al. |
| 5,376,337 A | 12/1994 | Seymour |
| 5,416,000 A | 5/1995 | Allen et al. |
| 5,504,013 A | 4/1996 | Senior |
| 5,576,009 A | 11/1996 | Nastke et al. |

(Continued)

FOREIGN PATENT DOCUMENTS

WO     WO-2021255268 A1     12/2021

*Primary Examiner* — Jennifer Wecker
*Assistant Examiner* — Jonathan Bortoli
(74) *Attorney, Agent, or Firm* — MUNCY, GEISSLER, OLDS & LOWE, P.C.

(57)     ABSTRACT

The present invention provides a test device. The device includes a testing element and a house configured to accommodate the testing element, where the house is formed by folding a paper-made card, and the testing element is located in the housing. The housing is allowed to be in different change states to test or assay an analyte in a sample.

16 Claims, 13 Drawing Sheets

(56) References Cited

U.S. PATENT DOCUMENTS

| | | | |
|---|---|---|---|
| 5,602,040 A | 2/1997 | May et al. | |
| 5,622,871 A | 4/1997 | May et al. | |
| 5,654,162 A | 8/1997 | Guire et al. | |
| 5,656,503 A | 8/1997 | May et al. | |
| 5,686,315 A | 11/1997 | Pronovost et al. | |
| 5,766,961 A | 6/1998 | Pawlak et al. | |
| 5,770,460 A | 6/1998 | Pawlak et al. | |
| 5,916,815 A | 6/1999 | Lappe | |
| 5,976,895 A | 11/1999 | Cipkowski | |
| 6,140,136 A | 10/2000 | Lee | |
| 6,187,269 B1 | 2/2001 | Lancesseur et al. | |
| 6,187,598 B1 | 2/2001 | May et al. | |
| 6,228,660 B1 | 5/2001 | May et al. | |
| 6,235,241 B1 | 5/2001 | Catt et al. | |
| 6,248,598 B1 | 6/2001 | Bogema | |
| 6,306,642 B1 | 10/2001 | Nelson et al. | |
| 6,352,862 B1 | 3/2002 | Davis et al. | |
| 6,372,515 B1 | 4/2002 | Casterlin et al. | |
| 6,379,620 B1 | 4/2002 | Tydings et al. | |
| 6,403,383 B1 | 6/2002 | Casterlin et al. | |
| 9,393,563 B2 | 7/2016 | Kim et al. | |
| 2003/0207466 A1* | 11/2003 | Po Lee | G01N 33/54366 |
| | | | 436/514 |
| 2004/0248322 A1* | 12/2004 | Charlton | G01N 33/54388 |
| | | | 436/514 |
| 2009/0232702 A1* | 9/2009 | Wu | G01N 33/54388 |
| | | | 422/400 |
| 2015/0251177 A1* | 9/2015 | Kim | B01L 9/06 |
| | | | 435/287.2 |
| 2016/0121322 A1 | 5/2016 | Fuller et al. | |
| 2023/0084255 A1 | 3/2023 | Shen et al. | |
| 2024/0189812 A1* | 6/2024 | Wu | G01N 33/54388 |

* cited by examiner

TEST DEVICE FOR DETECTING ANALYTE IN LIQUID SAMPLE

BACKGROUND OF THE INVENTION

Field of the Invention

The present invention relates to a device for collecting and testing a liquid sample, in particular, a device for collecting and testing an analyte in a liquid sample in the field of rapid diagnosis, such as a urine and saliva collection and testing device.

Description of the Related Art

The following description is merely an introduction of some background general knowledge and does not constitute any limitation to the present invention.

At present, the test device for detecting the presence or absence of an analyte in sample is widely used in hospitals or homes, and such test device for rapid diagnosis includes one or more detection reagent strips, such as early pregnancy detection and drug abuse detection. Such test device for rapid diagnosis is very convenient, and can obtain a test result from the detection reagent strips after one minute or no at most about ten minutes. Drug test is widely used by the drug control department, the Public Security Bureau, drug rehabilitation centers, physical examination centers, physical examination offices of national conscription, etc. The drug test is diverse and frequent. Some detections are required to collect samples and then samples are detected in professional testing agencies or testing laboratories, and some detections need to be completed in the site in time, for example, roadsides, for example, persons who drive after drug use need to be tested on the spot (referred to as "Drug Driving"), to obtain the test results in time.

For example, the detection of saliva samples is gradually accepted and favored by testing agencies or testing personnel due to convenient collection. In some literatures, various sample collection and test devices for clinical and domestic uses have been described. For example, the U.S. Pat. No. 5,376,337 discloses a saliva sampling device in which a piece of filter paper is used to collect saliva from the mouth of a subject and deliver saliva to an indicator reagent. U.S. Pat. Nos. 5,576,009 and 5,352,410 each disclose a syringe-type liquid sampling device.

For another example, a US patent application with the application number of Ser. No. 14/893,461 and publication number of US2016/0121322A1 discloses a test device for a sample; the patent only discloses some basic detection schemes and principles, and appears more difficult in the actual implementation of a specific product. For example, how to compress the pipet tip for absorbing saliva and how to move it if the cover body combination is matched with the detection combination, as well as how to mix with liquid effectively, the practical effects are undesirable.

At present, the in vitro detection of early pregnancy has been relatively mature, but still has many disadvantages, such as long detection time. In addition, such detection is usually operated by a test subject himself/herself, and still has many disadvantages, for example, inaccurate test results arising from proneness of mis-operation. It is desired that the existing OCT products are improved, so that the test results are generated in a short time, and the products fit with the operating habits of different operators.

In view of the above technical problems in some conventional products, it is necessary to improve them and provide an alternative approach to solve the drawbacks of the prior art.

BRIEF SUMMARY OF THE INVENTION

In view of the above situation, in order to overcome the disadvantages of the prior art, the object of the present invention is to provide a device for testing an analyte in a liquid sample. The device is especially suitable for testing HCG and LH in women, which can obtain test results quickly and reduce the inaccuracy of the test results due to the large amount of liquid. In addition, the device is suitable for operation by different operators.

This is because women directly urinate on a test device when tested for early pregnancy or ovulation, especially for a diversion element, which allows the diversion element to divert urine to the testing element for testing. Generally, women urinate directly on the diversion element. In this case, the testing element is held in the hand and the diversion element is placed under the urethra, so that urine directly drips onto the diversion element. Due to different operation habits and holding angles of operators, the amount of urine collected on the diversion element ranges from 1 ml to 200 ml, or more, for example, 500 ml. In addition, urine may also drip onto places beyond the diversion element, for example, the surface of the device. Generally, the amount of urine required for the testing element is not very large and much smaller than the amount of urine collected on the diversion element, and therefore the above many factors can affect the accuracy of the final test results.

In order to solve this problem, the present invention provides a test device. Especially when analytes such as HCG and LH in urine are tested, an operator can urinate directly on the test device for detecting them.

In one aspect, the present invention provides a test device for detecting an analyte in a liquid sample. The device includes a label-containing label pad, a lateral flow testing element having a nitrocellulose membrane in a testing area, and a housing having an upper housing and a lower housing, where one end of the label pad is overlapped on the nitrocellulose membrane, the testing element is located between the upper housing and the lower housing, one end of the housing is provided with an opening in which a part of a diversion element is located, and one end of the diversion element is in contact with the label area so that the liquid sample from the diversion element is capable of directly flowing to the label area.

In some embodiments, the other end of the diversion element is used for receiving a urine sample. In some embodiments, the other end of the diversion element is directly placed near the female urethra to receive the urine sample directly therefrom.

In some embodiments, the testing element is located in the lower housing in which a groove is disposed to accommodate the testing element. In some embodiments, the upper housing is provided with a liquid retention chamber which is capable of accommodating the liquid sample from the surface of the diversion element. Here, the liquid retention chamber has an opening covered by the diversion element, so that the liquid on the surface of the diversion element can flow to the liquid retention chamber. Therefore, in some embodiments, the chamber is one or more grooves with openings covering the surface of the diversion element. In some embodiments, these liquid retention chambers are non-capillary structured chambers, and the liquid sample is retained in the chamber depending on surface tension between the liquid and the chamber, rather than flowing. Therefore, the surfaces of the liquid retention chambers are treated with a hydrophilic material. Of course, if the liquid retention chambers have capillary force, the liquid sample is retained by them, rather than flowing, thereby reducing the level or volume of liquid on the surface of the diversion element. In some embodiments, the liquid retention chambers or the grooves are formed by spacing press strips, and the surface of the press strip covers the surface of the diversion element, so that excessive liquid flows to the liquid retention chambers. One function of the press strip is to limit the flow rate of the liquid on the surface of the diversion element, and the other function thereof is to allow the liquid to enter the liquid retention chambers. In this case, the liquid retention chambers may be non-capillary. Typically, the diversion element has an upper surface for receiving a liquid sample, a part of the diversion element is located inside the housing, and the other part thereof externally extends to receive the liquid.

In some embodiments, the device further includes a blocking element for blocking liquid at an end portion of the liquid outlet end of the diversion element from flowing to the label area, where the blocking element is disposed in the housing, and an end portion of the liquid outlet end of the diversion element is in contact with the blocking element. The blocking element may be any shape structure, for example, a sheet structure. The sheet structure is in contact with the liquid outlet end of the diversion element. In this way, the liquid from the diversion element is blocked by the blocking element, lowering the flow rate of the liquid flowing from the end portion and allowing the liquid to flow from the side of the diversion element, which decreases the flow of liquid and reduces the amount of the liquid. In some embodiments, the blocking element is disposed at an end portion of the liquid retention chamber or an end portion of the area where the liquid retention chamber is located, so as to block liquid on the diversion element from directly flowing to the label pad on the testing element and to allow the liquid to flow to the liquid retention chamber. In some embodiments, the blocking element is disposed on the upper housing, and the lower housing is provided with a recess, and the recess is provided with a blank area for a part of the label pad, and the end portion of the diversion element is located on the blank area and in direct contact with the blank area. In some embodiments, when the upper housing and the lower housing are assembled together, the blocking element is inserted into the recess and in contact with the end portion of the diversion element.

In some embodiments, the testing element further includes a sample application pad partially overlapped on the blank area on the label pad, the diversion element is overlapped on the sample application pad, and the flow rate of liquid on the diversion element is greater than that of liquid on the sample application pad.

In some embodiments, the testing element further includes a sample application pad partially overlapped on the blank area on the label pad, and the diversion element is overlapped on the sample application pad, where a part of liquid from the diversion element flows to the sample application pad, and a part of liquid from the diversion element directly flows to the label pad; and the time when the liquid from the diversion element directly flows to the label pad is earlier than the time when the liquid from the sample application pad flows to the label pad. In this way, the liquid from a detection reagent strip has two flow paths. One is the liquid sample directly from the diversion element, and the other is the liquid sample from the sample application pad. We hope that the liquid sample from the diversion element firstly contacts the label pad, and the liquid sample from the sample application pad is used as a subsequent liquid sample, so that there are test results in a short time, and the occurrence of false negatives can be reduced. Of course, if only the liquid from the diversion element directly flows to the label pad without the sample application pad, the structural design of the present invention can also result in obtaining the test results as soon as possible and reducing the number of false negatives or invalid test results.

In some embodiments, the label pad includes a first label pad and a second label pad, where the first label pad is located upstream of the second label pad, and the liquid outlet end of the diversion element is overlapped on the first label pad. In the present invention, two label pads are used to detect a same analyte, which can improve the detection sensitivity and shorten the detection time as compared with the conventional use of one label pad. In some embodiments, the first label pad includes a label-free blank area and a label-containing area, the second label pad includes a label-free blank area and a label-containing area, and the end portion of the diversion element is overlapped on the blank area of the first label pad. In some embodiments, the nitrocellulose membrane includes a test result area on which a second antibody specifically binds to the analyte is immobilized, and the label-containing area includes a first antibody that is conjugated with latex particles or/and gold particles and specifically binds to the analyte.

In some embodiments, the length of the label pad composed of the first label pad and the second label pad is 15 mm, the liquid outlet end of the diversion element is spaced from the label area of the first label pad by 2 mm, and the second label pad is spaced from the testing area by 7 mm. In this way, the distance that the liquid flows on the detection reagent strip is 24 mm, and the test results can be obtained within a very short distance, and are substantially controlled within 2 minutes. In some embodiments, the length of the diversion element is 40 mm, the length of the diversion element located in the housing is 13 mm, and the thickness of the diversion element is 3 mm.

In some embodiments, the second antibody specifically captures an HCG antigen, the first antibody specifically binds to the HCG antigen, and the sample is a urine sample. In some embodiments, the label on the first label pad is the first antibody that is conjugated with gold particles and binds to HCG in urine, and the label on the second label pad is the first antibody that is conjugated with latex particles and specifically binds to HCG in urine. These labels are dry and can flow with the liquid onto the test result area, and bind to the antibody immobilized on the test result area.

In some embodiments, the label pad includes a first label pad and a second label pad, where the first label pad is located upstream of the second label pad, and the liquid outlet end of the diversion element is overlapped on the first label pad. In some embodiments, the first label pad includes a label-free blank area and a label-containing area, the second label pad includes a label-free blank area and a label-containing area, and the end portion of the diversion element is overlapped on the blank area of the first label pad. In some embodiments, the length of the label pad composed of the first label pad and the second label pad is 15 mm, the liquid outlet end of the diversion element is spaced from the label area of the first label pad by 2 mm, the second label pad is spaced from the testing area by 7 mm, the length of the sample application pad is 15 mm, and the length of the diversion element is 40 mm, where the length of the diversion element in the housing is 13 mm.

BENEFICIAL EFFECT

The above structure can reduce the impact of excessive liquid samples on the accuracy of test results and obtain the test results quickly, which is especially suitable for women at home to self-test the concentration or level of HCG or LH in urine.

DETAILED DESCRIPTION OF THE INVENTION

Figure 1:
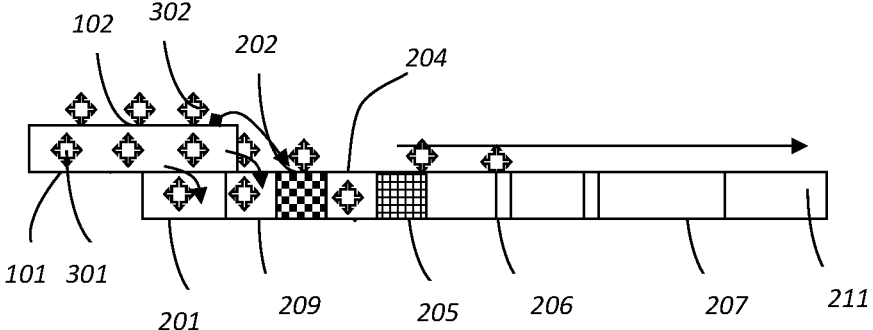
FIG. 1 is a schematic diagram showing the position relationship between a testing element and a diversion element in a housing of a test device according to an embodiment of the present invention (including a sample application pad 201).

The following further describes the structures involved in the present invention or the technical terms used therein. Unless otherwise specified, they shall be understood and explained according to the general terms commonly used in the prior art.

Detection

Detection means assaying or testing presence or absence of a substance or material, including but not limited to, chemical substance, organic compound, inorganic compound, metabolite, drug, drug metabolite, organic tissue, metabolite of organic tissue, nucleic acid, protein or polymer. In addition, detection means that the amount of a substance or material is tested. Further, assay also means immunoassay, chemical assay, enzyme assay, and the like.

Sample

The samples detected by the test device of the present invention include biological liquid (for example, case liquid or clinical sample). Liquid samples or fluid samples may be derived from solid or semi-solid samples, including feces, biological tissues and food samples. The solid or semi-solid samples may be converted to liquid samples by any appropriate methods, such as mixing, mashing, macerating, incubating, dissolving, or digesting the solid samples by enzymolysis in suitable solutions, such as water, phosphate solutions, or other buffer solutions. "Biological samples" include animal, plant, and food derived samples, including, for example, human or animal derived urine, saliva, blood and components thereof, spinal fluid, vaginal secretions, sperm, feces, sweat, secretions, tissues, organs, tumors, cultures of tissues and organs, cell cultures, and media. Preferably, the biological sample is urine, and preferably, the biological sample is saliva. Food samples include food processed materials, final products, meat, cheese, wine, milk, and drinking water. Plant samples include samples derived from any plants, plant tissues, plant cell cultures, and media. "Environmental samples" include samples derived from the environment (e.g., liquid samples from lakes or other bodies of water, sewage samples, earthen samples, groundwater, seawater, and waste liquid samples). The environmental sample may further include sewage or other waste water.

An appropriate test device according to the present invention can be used to detect any analyte. Preferably, the test device of the present invention is used to detect small drug molecules in saliva and urine. Of course, the samples detected by the test device of the present invention may be any samples of the above forms, regardless of being solid or liquid at the beginning, provided that these liquids or liquid samples can be absorbed by the sample application area of the testing element. Generally, the sample application area is made of a water absorbent material, and liquid samples or fluid samples can be absorbed by the capillary or other characteristics of the material of an absorption element, so that the liquid sample can flow in the sample application area. The material of the sample application area may be any material capable of absorbing liquid, such as sponge, filter paper, polyester fiber, gel, non-woven fabric, cotton, polyester film, and yarn. Of course, the sample application area may be made of a water absorbent material or a non-water absorbent material. However, the absorption element is provided with holes, screw threads, and caves on which the samples can be collected. Generally, the samples are solid or semi-solid samples, and filled between screw threads and in the holes or caves for collection. Of course, optionally, the sample application area may be composed of some non-absorbent fibers and hairs, and these materials are used to scrape a solid, semi-solid or liquid sample, so that these samples can be retained on the sample application area. If detection is needed, a buffer solution is applied to the sample application area to dissolve the sample, so that the dissolved sample flows on the testing element or the detection element.

In some embodiments, the liquid sample contacts the diversion element, instead of being manually applied to the sample application area of the testing element of the present invention, so that the liquid sample diverted by the diversion element flows to the sample application area and the label area sequentially, followed by being assayed or tested. The following further gives a detailed description with reference to the specific embodiments. In some embodiments, the liquid sample diverted by the diversion element flows directly onto the label area, without passing through the sample application area. In some embodiments, a part of liquid sample flowing to the label area is from the sample application area, while s a part of liquid sample is directly from a diversion area. In some embodiments, the samples in the sample application area are from the diversion element. In some embodiments, the diversion element is used to receive the liquid sample. For example, during detection, women urinate directly on the diversion element, and then the test results are observed.

Downstream and Upstream

Downstream or upstream is divided according to a flow direction of a liquid, generally, a liquid or fluid flows to a downstream area from an upstream area. The downstream area receives the liquid from the upstream area, and a liquid also may flow to a downstream area along an upstream area. Here, downstream or upstream is generally divided according to a flow direction of a liquid, for example, on some materials where capillary force is utilized to promote the flow of a liquid, a liquid may overcome gravity to flow towards an opposite direction to the gravity; and in this case, downstream or upstream is divided according to a flow direction of the liquid. For example, in the test device of the present invention, after the diversion element receives a liquid sample, for example, a urine sample directly from a test subject, fluid can flow from the diversion element to the label area, for example, a first gold particle label area, to a second latex label area, and then to a testing area, for example, a test result area and a test result control area. In this case, the liquid on the diversion element flows to the first label area, the second label area, and then the test result area. Flow from a diversion area to a testing area is from upstream to downstream. In a flow process, the liquid passes through the first label area and the second label area sequentially, and the testing area includes a test result area and a test result control area. The testing area may be a polyester fiber film, and the diversion element may be a glass fiber, a polyester chip, and a polyester film. In this case, the diversion element is located at the upstream of the label area of the testing element. The specific structure of the testing element 20 is as shown in FIGS. 1-2.

Gas Flow or Liquid Flow

Gas flow or liquid flow means that liquid or gas can flow from one place to another place. In a flow process, the liquid or gas may pass through some physical structures to play a guiding role. The "passing through some physical structures" here means that liquid passes through the surface of these physical structures or their internal space and flows to another place passively or actively, where passivity is usually caused by external forces, such as flow under the capillary action and the action of air pressure. The flow here may also be a flow due to self-action (gravity or pressure) of the liquid or gas, and also may be a passive flow. The fluid under the action of air pressure may be a forward flow, or also a reverse flow; or a fluid is urged to flow to another position from a position under the action of air pressure. Here, the flow does not mean that a liquid or a gas is necessarily present, but indicates a relationship or state between two objects under some circumstances. In case of presence of liquid, it can flow from one object to another. Here it means the state in which two objects are connected. In contrast, if there is no gas flow or liquid flow state between two objects, and liquid exists in or above one object but cannot flow into or on another object, it is a non-flow, non-liquid or non-gas flow state.

Testing Element

The "testing element" used herein refers to an element that can be used to detect whether a fluid sample or a fluid specimen (a liquid sample or a liquid specimen) contains an interested analyte. Such testing can be based on any technical principles, such as immunology, chemistry, electricity, optics, molecular science, nucleic acids, and physics. The testing element can be a lateral flow detection reagent strip that can detect a variety of analytes. Of course, other suitable testing elements can also be used in the present invention.

Various testing elements can be combined for use in the present invention. One form of the testing elements is a test paper. The test papers used for analyzing the analyte (such as drugs or metabolites that show physical conditions) in samples can be of various forms such as immunoassay or chemical analysis. The analysis mode of non-competition law or competition law can be applied for test papers. A test paper generally contains a water absorbent material that has a sample application area, a reagent area, and a testing area. Fluid or liquid samples are added to the sample application area and flow to the reagent area under the capillary action. If analyte exists in the reagent area, samples will bind to the reagent. Then, samples continue to flow to the testing area. Other reagents such as molecules that specifically bind to analyte are immobilized on the testing area. These reagents react with the analyte (if any) in the sample and bind to the analyte in this area, or bind to a reagent in the reagent area. Label used to display the detection signal exists in the reagent area or the detached label area.

Typical non-competition law analysis mode: if a sample contains analyte, a signal will be generated; and if not, no signal will be generated. Competition law: if no analyte exists in the sample, a signal will be generated; and if analyte exists, no signal will be generated.

The testing element can be a test paper, which can be water absorbent material or non-water absorbent material. The test paper can contain several materials used for delivery of liquid samples. One material can cover the other material. For example, the filter paper covers the nitrocellulose membrane. One or more materials may be used in one area of the test paper, and one or more other different materials may be used in the other area thereof. The test paper can stick to a certain support or on a hard surface for improving the strength of holding the test paper.

Analyte is detected through a signal generating system. For example, one or more enzymes that specifically react with this analyte is or are used, and the above method of fixing a specific binding substance on the test paper is used to fix the combination of one or more signal generating systems in the analyte testing area of the test paper. The substance that generates a signal can be in the sample application area, the reagent area or the testing area, or on the whole test paper, and one or more materials of the test paper can be filled with this substance. The solution containing a signifier is added onto the surface of the test paper, or one or more materials of the test paper is or are immersed in a signifier-containing solution. The test paper containing the signifier solution is made dry.

Various areas of the test paper can be arranged as follows: sample application area 201, reagent area 202, 204, and testing area 207, where the testing area includes a test result area 206 and a test result control area 210. The test result control area is located behind the testing area. All areas can be arranged on a test paper that is only made of one material. Alternatively, different areas may be made of different materials. Each area can be in direct contact with the liquid sample, or different areas are arranged according to the flow direction of liquid sample; and a tail end of each area is connected and in overlapped with the front end of the other area. Materials used can be those with good water absorption such as filter papers, glass fibers or nitrocellulose membranes. The test paper can also be in other forms.

Figure 2A:
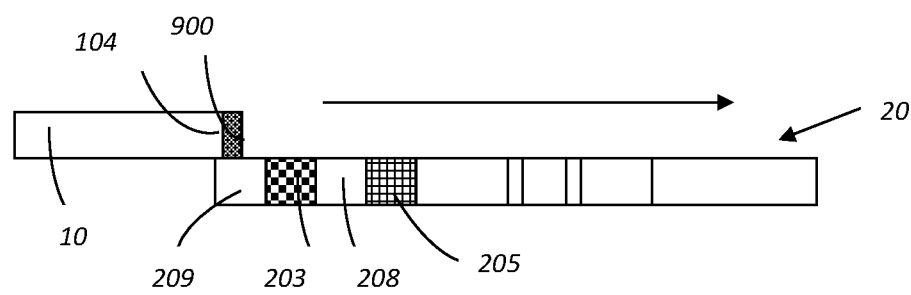
FIG. 2A is a schematic structural diagram of a diversion element and a testing element according to the present invention, where a blocking element 900 is located at an end portion of the diversion element, and the end portion of the diversion element directly overlaps with a blank area of a first label pad 202.

The nitrocellulose membrane detection reagent strip is commonly used, that is, the testing area includes a nitrocellulose membrane (NC) on which a specific binding molecule is immobilized to display the test result; and other detection reagent strips such as cellulose acetate membrane or nylon membrane detection reagent strips can also be used. For example, detection reagent strips and similar devices with detection reagent strips disclosed in the following patents: U.S. Pat. Nos. 4,857,453; 5,073,484; 5,119,831; 5,185,127; 5,275,785; 5,416,000; 5,504,013; 5,602,040; 5,622,871; 5,654,162; 5,656,503; 5,686,315; 5,766,961; 5,770,460; 5,916,815; 5,976,895; 6,248,598; 6,140,136; 6,187,269; 6,187,598; 6,228,660; 6,235,241; 6,306,642; 6,352,862; 6,372,515; 6,379,620, and 6,403,383. The detection reagent strips and similar device with detection reagent strips disclosed in the above patents may be applied to the testing element or test device of the present invention for the detection of an analyte, for example, the detection of an analyte in a sample.

detection reagent strips used in the present invention may be commonly referred as lateral flow detection reagent strips. The specific structure and detection principle of the detection reagent strips are well known to a person skilled in the art in the prior art. A common detection reagent strip (as shown in FIGS. 1-2) includes a sample collection area or a sample application area 201, a label area (202, 204), and a testing area 207; the sample collection area includes a sample receiving pad, the label area includes a label pad, and a water absorbent area may include a water absorbent pad, where the testing area includes necessary chemical substances for detecting the presence or absence of analyte, such as immunoreagents or enzyme chemical reagents. The sample application area or application pad 201 of the present invention is in contact with the diversion element to receive liquid sample diverted by g it, rather than directly receiving the sample. Therefore, the sample application area of the present invention is covered by the diversion element (as shown in FIG. 1). Of course, as shown in FIG. 2A, the detection reagent strip has no a sample application area. The nitrocellulose membrane detection reagent strip is commonly used, that is, the testing area 207 includes a nitrocellulose membrane, and an area 206 (T-line) on which a specific binding molecule is immobilized to display the test result; and other detection reagent strips such as cellulose acetate membrane or nylon membrane detection reagent strips can also be used. Of course, in the downstream of the testing area, there may also be a test result control area 210 (C-line); generally, detection reagent strips appear on the test result control area and the testing area in the form of a horizontal line, namely, a test line or a control line. Such detection reagent strips are conventional. Of course, they can also be other types of detection reagent strips for detection under the capillary action. In addition, there are dry chemical reagent components on common detection reagent strips, for example, an immobilized antibody or other reagents. When the detection reagent strip contacts liquid, the liquid flows along the detection reagent strip under the capillary action, and the dry reagent components are dissolved in the liquid and treated in a next area, and the dry reagents react in the area for necessary detection. The liquid flow mainly relies on the capillary action. Here, all of the detection reagent strips can be applied to the test device of the present invention or can be disposed in contact with the liquid samples in a detection chamber or used to detect the presence or absence of analyte in the liquid samples that enter a detection chamber, or the quantity thereof.

In addition to the foregoing detection reagent strip or lateral flow detection reagent strip which is used to contact with the liquid sample to test whether the liquid samples contain analytes. The testing element of the present invention may be used as a test device by itself to detect an analyte in a sample. Therefore, the test device here is equal to a testing element. For example, after being mixed with a treatment solution, the fluid sample is detected with a testing element directly, specifically described as follows: when a receiving device is described to treat a fluid sample, the testing element may be used for detection alone. In the present invention, the detection reagent strip only includes the label area and the testing area, without the sample application area 201. In some embodiments, the label area of the testing element of the present invention includes a first label area and a second label area both which have a label, for example, a color particle label or a conjugated antibody, where the antibody can specifically bind to an analyte in a sample. In some embodiments, the first label area is located upstream of the second label area, and color particles conjugated with the antibody in each label area are different. In some embodiments, the color particles may be latex particles, gold particles, or dye particles.

Analyte

Examples that can use an analyte related to the present invention comprise small-molecule substance, including drugs (such as drug of abuse). "Drug of Abuse" (DOA) refers to using a drug (playing a role of paralyzing the nerves usually) not directed to a medical purpose. Abuse of these drugs will lead to physical and mental damage, dependency, addiction and/or death. Examples of drug abuse include cocaine; amphetamine (AMP) (e.g., Black Beauty, white amphetamine tablets, dexamphetamine, dexamphetamine tablets, and Beans); methamphetamine (MET) (crank, meth, crystal and speed); barbiturate (BAR) (such as Valium, Roche Pharmaceuticals, Nutley, and New Jersey); sedatives (i.e., a sleep aid medicine); lysergic acid diethylamine (LSD); inhibitors (downers, goofballs, barbs, blue devils, yellow jackets, and methaqualone); tricyclic antidepressants (TCAs, i.e. imipramine, amitriptyline, and doxepin); dimethylenedioxymethylaniline (MDMA); phencyclidine (PCP); tetrahydrocannabinol (THC, pot, dope, hash, weed, etc.); opiates (i.e., morphine (MOP) or opium, cocaine (COC), heroin, and hydroxydihydrocodeinone); and anxiolytic drugs and sedative-hypnotic drugs. The anxiolytic drugs are mainly used for relieving anxiety, tension, and fear, and stabilizing emotion, and have hypnotic and sedative effects. The anxiolytic drugs include benzodiazepines (BZO), atypical benzodiazepines (BZ), fused dinitrogen NB23C, benzodiazepines, ligands of BZ receptors, open-ring BZ, diphenylmethane derivatives, piperazine carboxylates, piperidine carboxylates, quinazolinones, thiazine and thiazole derivatives, other heterocycles, imidazole-type sedative/analgesic drugs (e.g., oxycodone (OXY) and methadone (MTD)), propylene glycol derivatives-carbamates, aliphatic compounds, anthracene derivatives, and the like. The detection device of the present invention may also be used for detecting drugs belonging to a medical use but easy to be taken excessively, such as tricyclic antidepressants (imipramine or analogues) and acetaminophen. These drugs are metabolized into micromolecular substances after absorbed by human body. These micromolecular substances exist in blood, urine, saliva, sweat and other body fluids or in some body fluids.

For example, the analyte detected by the present invention includes but is not limited to creatinine, bilirubin, nitrite, (nonspecific) proteins, hormones (for example, human chorionic gonadotropin, progesterone, follicle-stimulating hormone, etc.), blood, leucocytes, sugar, heavy metals or toxins, bacterial substances (such as proteins or carbohydrates against specific bacteria, for example, *Escherichia coli* 0157:H7, *Staphylococcus, Salmonella, Fusiformis, Campylobacter* genus, *L. monocytogenes, Vibrio*, or *Bacillus cereus*) and substances related with physiological features in a urine sample, such as pH and specific gravity. Chemical analysis of any other clinical urine may be performed by lateral flow detection in combination with the device of the present invention.

The sample of the present invention may be urine, and the analyte may be HCG, LH, and other substances, which are used for testing ovulation or early pregnancy.

Housing Including Testing Element

In some specific embodiments, the testing element may be also disposed on some carrier elements; the carrier elements include the testing element to complete the detection and assay of the analytes in fluid samples. Therefore, in some embodiments, the test device includes a carrier, and the carrier is provided with a testing element. In some embodiments, the carrier of the present invention is a housing used for bearing or accommodating the testing element; the carrier element does not participate in the detection directly by itself, but serves as a carrier or housing used for bearing or accommodating the testing element. In some embodiments, the housing or carrier of the present invention includes a groove structure 901, and the structure is used for limiting the position of the testing element on the carrier. One or more groove structures here may be available. Each groove is provided with a testing element, and the testing element may be used for testing the number or presence of analytes in a sample.

Figure 3:
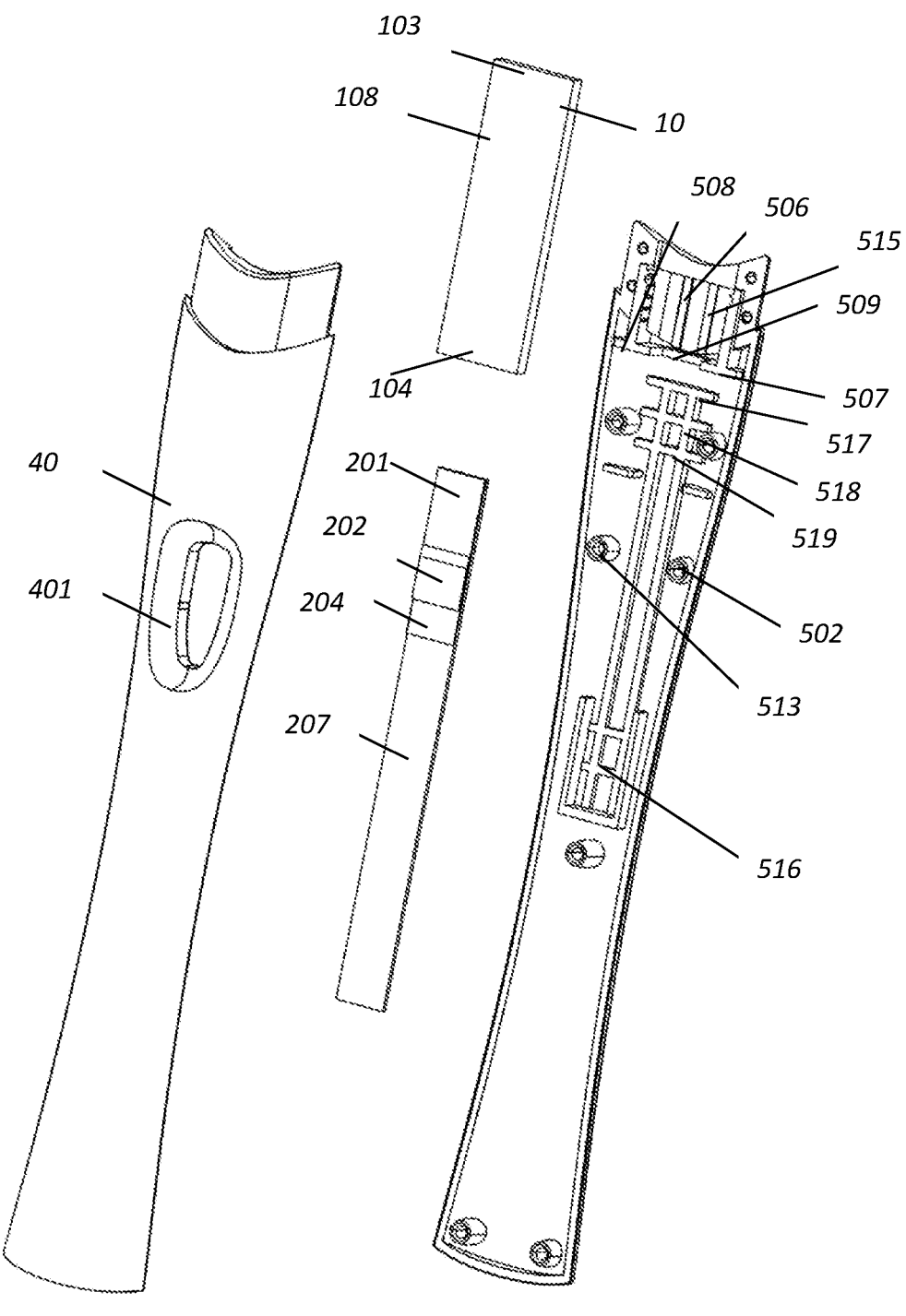
FIG. 3 is a schematic diagram showing a three-dimensional structure of a test device according to an embodiment of the present invention.
Figure 4:
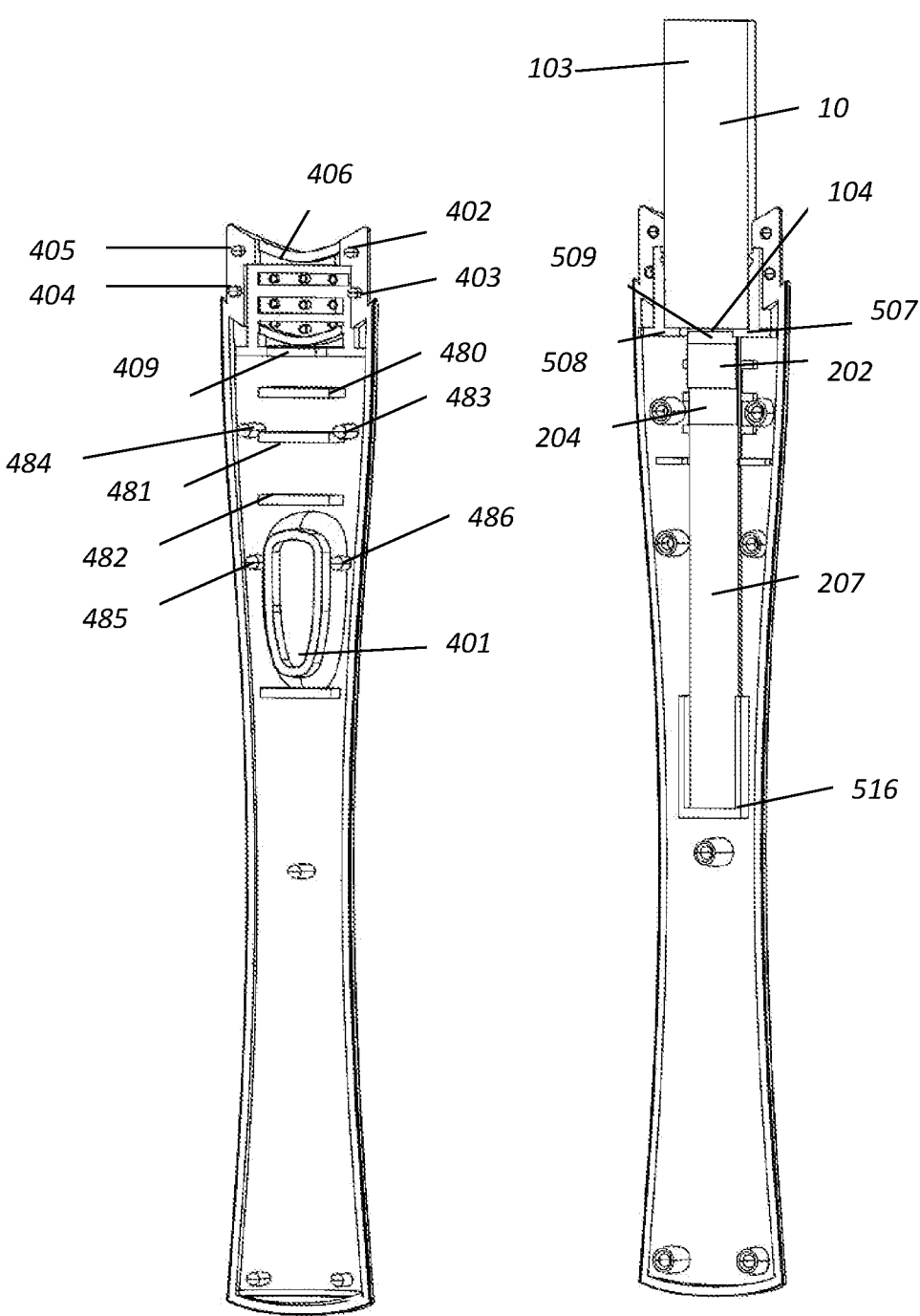
FIG. 4 is a schematic diagram of a lower housing including a testing element and an upper housing according to an embodiment of the present invention.
Figure 5:
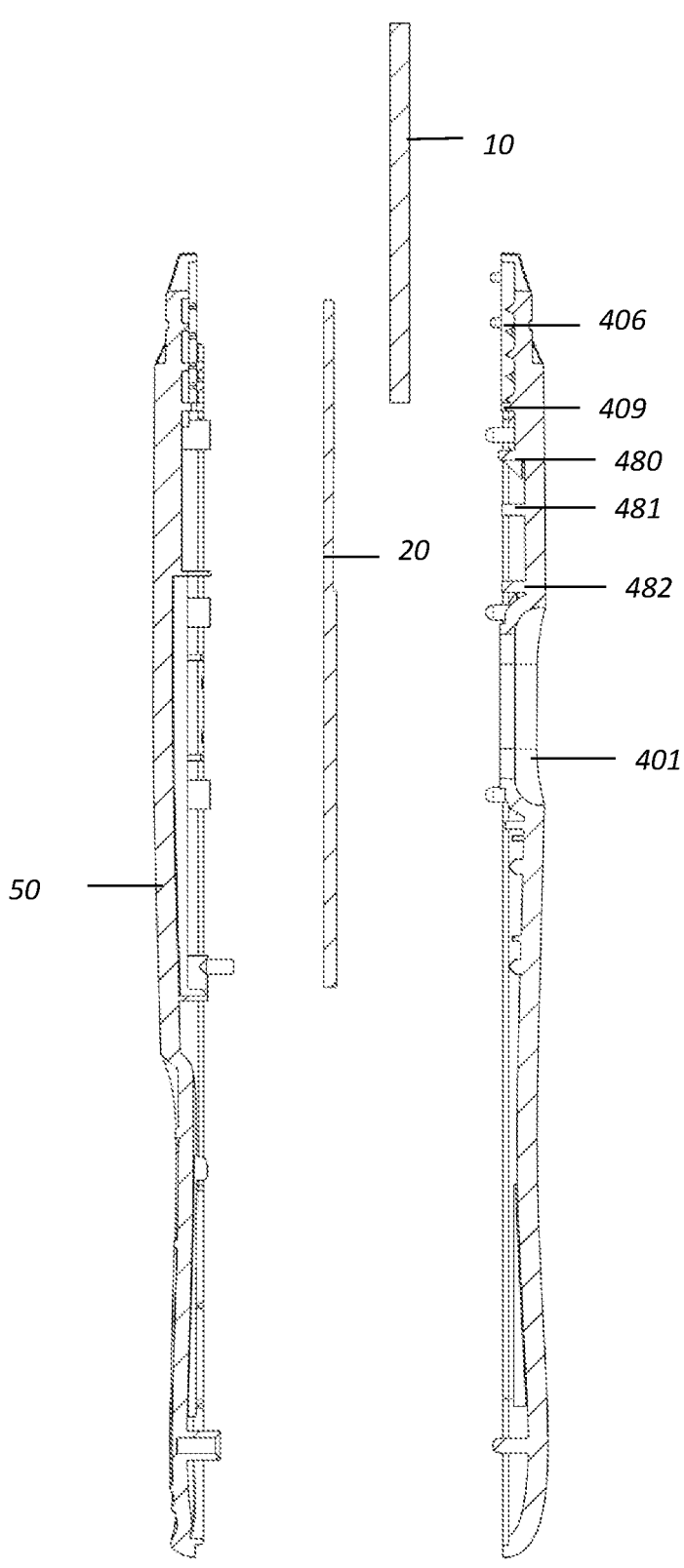
FIG. 5 is a schematic diagram showing a longitudinal cross-section structure of a test device in an assembly state according to an embodiment of the present invention.

In some embodiments, as shown in FIGS. 3-8, the test device includes a testing element 20, an upper housing 40, and a lower housing 50, and the upper housing and the lower housing can also be called an upper plate and a lower plate. As shown in FIG. 3, the test device includes the upper housing 40 and the lower housing 50. The lower housing is provided with a groove on which the testing element 20 is disposed, the groove is provided with several support strips, the overall width of the groove is consistent with the opening end of the testing element, and then the groove is covered with the upper housing to form the test device. As shown in FIG. 5, when the width of the groove 516 in the lower housing 50 is the same as that of the testing element, and a plurality of support strips are disposed on the groove and parallel to or perpendicular to the detection reagent strip. For example, one end of the housing is provided with three support strips 517, 518 and 519 perpendicular to the longitudinal direction of the detection reagent strip. The three support strips are corresponding to three press strips 480, 481 on the upper housing 40 (one of which is not shown), and press several areas on the detection reagent strip or the overlapping places of several reagent pads respectively, so that the reagents on the reagent pads can be released evenly and the phenomenon of "flooding" can be prevented. This will be explained in detail in combination with embodiments.

In some embodiments, the lower housing is further provided with an area for placing the diversion element 10, one end of the diversion element is placed on the area, and the other end thereof protrudes from the housing to receive a fluid sample. The upper housing is further provided with an area 406, when pins 405, 402, 404, 403 of the upper housing are combined with sockets 505, 502, 503, 504 of the lower housing 50, one end of the diversion element is located in the area. The area 406 of the upper housing is located on the upper surface 108 of the diversion element, and the area of the lower housing is located under the lower surface of the diversion element, so that part of the diversion element is located in the housing, and the part protruding from the housing is used to receive the liquid sample. When especially used for receiving female urine directly, the diversion element has two functions, one is to directly receive female urine, and the other is to transmit it to the testing element 10 to detect and array the presence or absence or quantity of analytes in urine, such as HCG and LH. Such an area on the lower housing 50 is also a sample application area that can be used to place the testing element, and provided with support strips 506, 515 which are used to support the sample application area 201. A partition is disposed between the support area of the sample application area and the reagent area or label area 203, 204 for supporting the detection reagent strip. A groove or recess 509 is arranged in the middle of the partition, to separate the label area from the sample application area. The partition is divided into two parts 507, 508 by the recess 509. The width of the recess or groove is consistent with that of the detection reagent strip. The width of the sample application area on a support testing element 20 is smaller than that of the diversion element. When the diversion element is placed in the application area 201 of the support testing element, the diversion element 10 covers the sample application area or the sample application pad 201, but the liquid outlet end of the diversion element is in overlapped contact with the label pad 202. It can be understood that the testing element is of an integral structure. After assembly, it is placed together in the groove 501 of the lower housing. A part of the testing element passes through the recess 509, and the sample application pad 201 is located in the area where the support strips 506, 515 of the lower housing are located. Then, the diversion element 10 is placed at the front end of the partition, so that the tail end 104 (liquid outlet end) of the diversion element is in contact with the front surfaces of the partitions 507, 508. In some embodiments, the width of the recess 509 is the same as that of the testing element, but the width of the diversion element is larger than that of the testing element. Therefore, the tail end 104 (liquid outlet end) of the diversion element is limited by the partitions 507,508, so that the upper surface 108 of the tail end of the diversion element is abutted against the partitions. In this way, a part of liquid from the diversion element 10 flows to the sample application area 201 of the testing element, and then flow to the label pad through the sample application area, and the part of liquid flows directly from the diversion element to the label pad. Therefore, when the detection reagent strip is placed in the groove 516 of the lower housing, and if the sample application pad 201 is absent, the blank area of the label pad 202 slightly passes through the recess about 1-2 mm, so that the liquid outlet end 104 of the diversion element is in contact with the label pad, allowing the liquid to directly flow onto the label pad.

In this embodiment, because the aperture of the diversion element is relatively large and liquid directly contacts the diversion element firstly, there is more liquid on the diversion element. The liquid flows from the liquid outlet end 104 of the diversion element to the label pad to contact and dissolve the label reagent thereon, and the dissolved label reagent flows forward, and then the liquid from the sample application area flows to the label area to contact and dissolve the label reagent thereon. The liquid in the sample application pad 201 (if any) is also from the diversion element, which can accelerate liquid flow and shorten the liquid flow distance. In this way, for example, as shown in FIG. 1, the tail end 104 of the diversion element is also overlapped on the label area, so that the liquid can flow in advance to quickly reach the testing area (T line) and early obtain the test result. Therefore, in an embodiment, the liquid from the diversion element 10 reaches the label area earlier than the liquid from the sample application pad 201. In other words, the label pad receives the liquid from the diversion element earlier than the liquid from the sample application pad. One way to improve the above case is that the flow guide element has large aperture and loose texture, and the sample application pad has small aperture and tight texture, thereby causing difference in the flow rate of liquid. In some embodiments, the flow rate of the liquid in the diversion element is greater than that of the liquid in the sample application pad. The liquid herein may include a urine sample. In this way, with two different liquids flowing to the testing element, the liquids can flow on the testing element in advance, thereby accelerating moistening of a dry reagent (label) under the action of a liquid sample and allowing the analyte in the liquid sample to react with the label. It is well known in the art that surface reaction can be carried out only under a moistening condition, for example, a label-conjugated antibody can specifically bind to the analyte, such as HCG or LH.

In some embodiments, the testing element may only include the label area and the testing area without the sample application area 201, and the tail end (label) of the testing element is limited by the partition. Therefore, it can be understood that the label area can reach the recess 509 at most or slightly extends out of it. For example, the blank area 209 of a first label pad protrudes from the recess 509 by 1-3 mm, and the protruding part is covered by the diversion element. However, the lower housing for supporting the tail end of the diversion element only includes diversion element, without any components on the detection reagent strip and the liquid application pad 201, and the tail end 104 of the diversion element is in contact with the blank end 209 of the label area. In this way, the liquid from the diversion element can flow onto the label pad directly to release the solution of the label on the label pad, thus achieving detection. In this way, the liquid does not flow to the sample application area on the detection reagent strip and the liquid on the diversion element is not diverted. This shortens the distance that the liquid flows on the detection reagent strip and accelerates the display of test results.

Figure 2B:
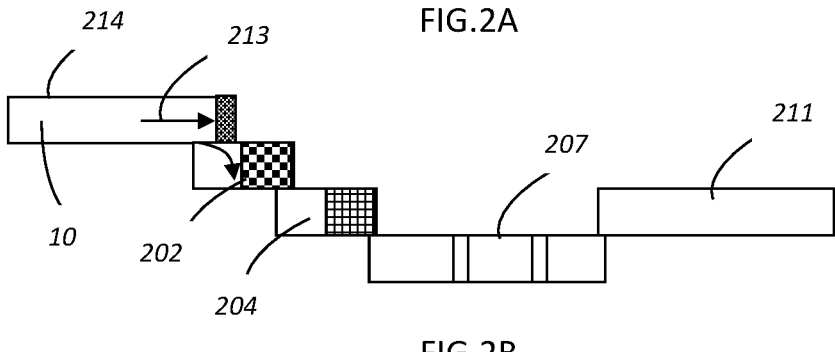
FIG. 2B is a schematic diagram showing an assembling structure of each pad according to the present invention.

The label area of the detection reagent strip includes a first label pad 202 and a second label pad 204, where the first label pad 202 has an area 203 with a label reagent and a blank area 209 without a label reagent. When the diversion element covers the sample application area 201, the tail end of the diversion element covers the sample application area to indirectly cover the blank area 209 without a label reagent (as shown in FIGS. 2A-2B). In this way, the liquid from the diversion element can also flow directly to the blank area 209 on the label pad 202. The diversion element covers the sample application area 201 (if any), and then one end of the sample application area covers the blank area 209 without a label reagent. Therefore, one end 104 of the diversion element 10 covers the sample application area 201 to indirectly cover the blank area 209 of the label pad, so that a part of liquid from the diversion element flows to the sample application area and a part of liquid from the diversion element directly flows to the blank area 209 of the label area. As mentioned above, the flow rate of the liquid from the diversion element is faster than that of the liquid from the sample application area, and the diversion element firstly contacts the liquid. Therefore, the liquid from the diversion element firstly flows to the label area.

In some embodiments, the detection reagent strip includes the sample application area 201 that is overlapped with the blank area 209 of the first label area 202, the first label area 206 of the first label area is overlapped with the blank area 208 of the second label pad 204, the area 205 including the second label on the second label area is overlapped with the testing area 207 located on the nitrocellulose membrane. The testing area includes a test result area 206 and a test result control area 210. Generally, the test result area is linear, such as T line 206, and the control area is also linear, abbreviated as C line 210. Antibodies are treated on the T line and the C line and immobilized. The T line is used to capture an analyte, while the antibodies on the area where the C line is located are used to capture a label. Generally, the appearance of a line on the C line represent the effectiveness of the test result, while the color depth of a line on the T line represents the amount of the analyte and its presence or absence.

In some embodiments, a first label and a second label are an antibody marked with gold particles and an antibody marked with latex particles, respectively. These antibodies are specific to a same analyte. For example, if it is desired to test HCG in urine, the first label is the first anti-HCG antibody conjugated with gold particles, and the second label is the first anti-HCG antibody conjugated with latex particles HCG. The antibody here may be mouse anti-HCG or goat anti-HCG, and the second anti-HCG antibody is immobilized on the T line. The first antibody and the second antibody bind to different sites on HCG respectively. Of course, it can be understood that both the first label and the second label are marked with gold particles or latex particles, but conjugated with the antibody of a same analyte.

In some embodiments, the label further includes a first anti-human IgG antibody, and a second antibody capturing human IgG is immobilized on the C line. Regardless of the presence or absence of the analyte in the urine, a line appears on the C line. However, if there is a flooding phenomenon, no line appears on the C line sometimes. To solve the flooding phenomenon, the test device of the present invention is structurally improved and can quickly detect results within 2 minutes, for example, 1-2 minutes, so that the test results can be known earlier.

There are generally several ways to obtain the test results quickly or make the color lines appear in the T line area faster. For example, on the one hand, it is necessary to shorten the distance that the liquid flows on the detection reagent strip (especially the distance from the label area to the test result area (the position of the T line) as short as possible), so that it is desired that the sample liquid reaches the label area at the fastest speed. On the other hand, the large amount of liquid results in accelerating the flow rate and obtaining the test results early. However, it is difficult to achieve the actual situation. Due to the short distance of liquid flow, it is not an easy thing to make the dry reagent quickly dissolved in the liquid sample and react them fully in a short distance. Although the large amount of liquid results in accelerating the flow rate, there is a flooding phenomenon, that is, the liquid quickly flows from the surfaces of the label pads on the detection reagent strips to moisten the testing area in advance, instead of materially flowing from the label pads, so that the label subsequently dissolved is difficult to reach the testing area and no test results are displayed on the testing area (which has been moistened). When the above two aspects are needed, it is desired to find a balance to shorten the distance of liquid flow without impact on the reagent reaction which should be sufficient. If the amount of the liquid is increased, it should not be increased too much so as to avoid the flooding phenomenon caused by too much liquid, which leads to the failure of effective detection. This is exactly the problem that the present invention hopes to solve. If too much liquid is present on the testing element and its flow rate is too fast, or the flow rate of the liquid flowing onto the surface of the testing element is greater than that of the liquid flowing into the testing element under the capillary action, the test results are inaccurate.

During the detection of a lateral flow test, the liquid flows under the capillary force, and reaction between reagents during liquid flow generates results, such as binding reaction between an antibody and an antigen. When the liquid flows quickly from the surface of the detection reagent strip (substantially not relying on the capillary force), it moistens the downstream area in advance, without effectively dissolving the dry reagent on the detection reagent strip. For example, if the liquid on the label pad flows quickly from the surface of the label area (at the large amount of liquid), it does not dissolve the dry reagent on the label area but reaches the testing area, for example, the nitrocellulose membrane, thereby moistening the nitrocellulose membrane in advance. As a subsequent reagent or solution in which the reagent is dissolved cannot flow or reach the testing area, the desired reaction cannot be caused and accordingly the detection cannot be effectively achieved. This is because, after the testing area is moistened in advance, the capillary force therein disappears or decreases, so that a subsequent liquid cannot continue to flow under the capillary action. If the nitrocellulose membrane is moistened in advance, a label-containing solution cannot continue to flow under its capillary action, so that it may not flow to the testing area, which eventually leads to the failure of detection, for example, the T line does not display color or has no color (when the sample is positive), and even the downstream C line has no color with an invalid structure. This is caused by too much liquid instead of insufficient liquid.

In order to shorten the distance of liquid flow, one solution of the present invention is that the liquid outlet end 104 of the diversion element 10 is directly overlapped with the blank area 209 of the label area (as shown in FIG. 2A), the length of the label area is 10-20 mm, the label area is spaced from the T line area by 6-10 mm, and the distance of liquid flowing on the detection reagent strip is about 16-30 mm, so that the test results are quickly generated on the T line due to the relatively short distance. This way has been explained above. If the testing element does not include the sample application area, the liquid on the diversion element flows directly to the label area so that the liquid can reach the detection reagent strip quickly. If the testing element includes the sample application area 201, the sample application area is shortened, for example, within 10 mm, and the tail end 104 of the diversion element is in contact with the label pad, so that at least part of the liquid reaches the label pad firstly. The liquid on a conventional testing element needs to flow the label area from the sample application area, some sample application areas are up to 20-80 mm long, and the total distance of the liquid flowing from sample application area to the label area is 40-120 mm. Test results can be determined usually after 5 minutes.

Another solution of the present invention is that liquid is desired to flow in such a short distance. If the label reagent is distributed in one area, its amount is relatively large. When the liquid passes through the area, a dry label needs to be dissolved in the liquid and accurate test results can be obtained with liquid flow. If the distance of liquid flow is short, it is desired that the label is quickly dissolved by the liquid. When the amount of the label is large, the dry label cannot be fully dissolved in the liquid and fully bind to an analyte in a sample, thereby causing inaccurate test results, for example, false negative results. In order to overcome this problem, the labels of the present invention are respectively placed on two label pads 202, 204 overlapped with each other. Liquid flows on the label pads through a blank area gap 208, for example, 2-3 mm. Because the labels are placed on the label pads, no many labels are present in each area. The labels in one conventional label area are shared by two label areas so that liquid can more fully contact a dry label in a flowing process and a solution can dissolve more labels in a short time, thereby improving the detection accuracy or sensitivity. Especially for the detection of HCG of early pregnancy, it is desired that an early detection indicates a good detection effect, so that the test result can be known in advance and the detection accuracy is not affected.

In addition, it is desired that the liquid flowing to the testing element is maximized and its flow rate also can be accelerated, without the flooding phenomenon, to ensure that test results are generated in a short time. Otherwise, invalid test results are generated. For example, for positive urine (HCG), no line appears on the T line, or no line appears on the T line or C line, or a line appears only on the T instead of the C line, and the test results are invalid.

Figure 9:
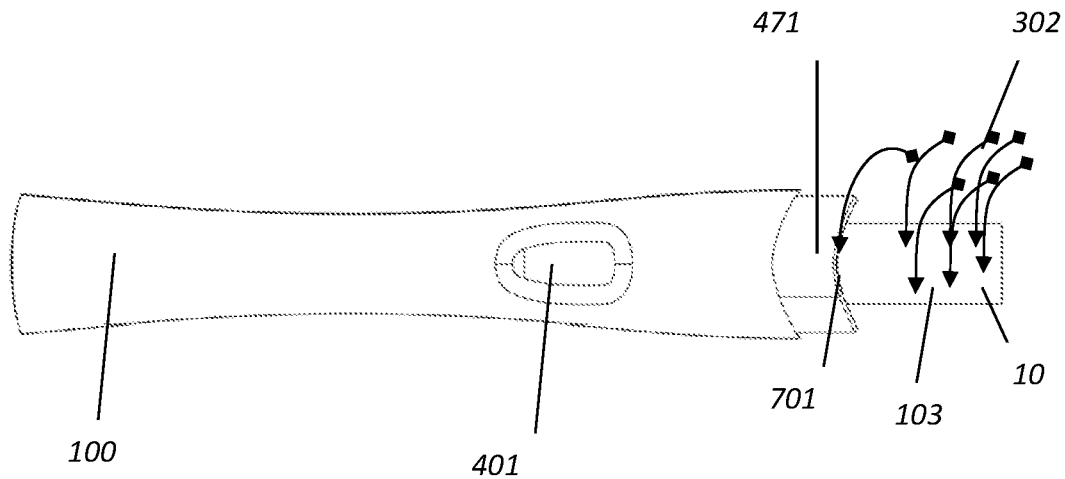
FIG. 9 is a schematic diagram showing an operation state of a test device for receiving a urine sample and a diversion element for receiving a urine sample according to an embodiment of the present invention.
Figure 10:
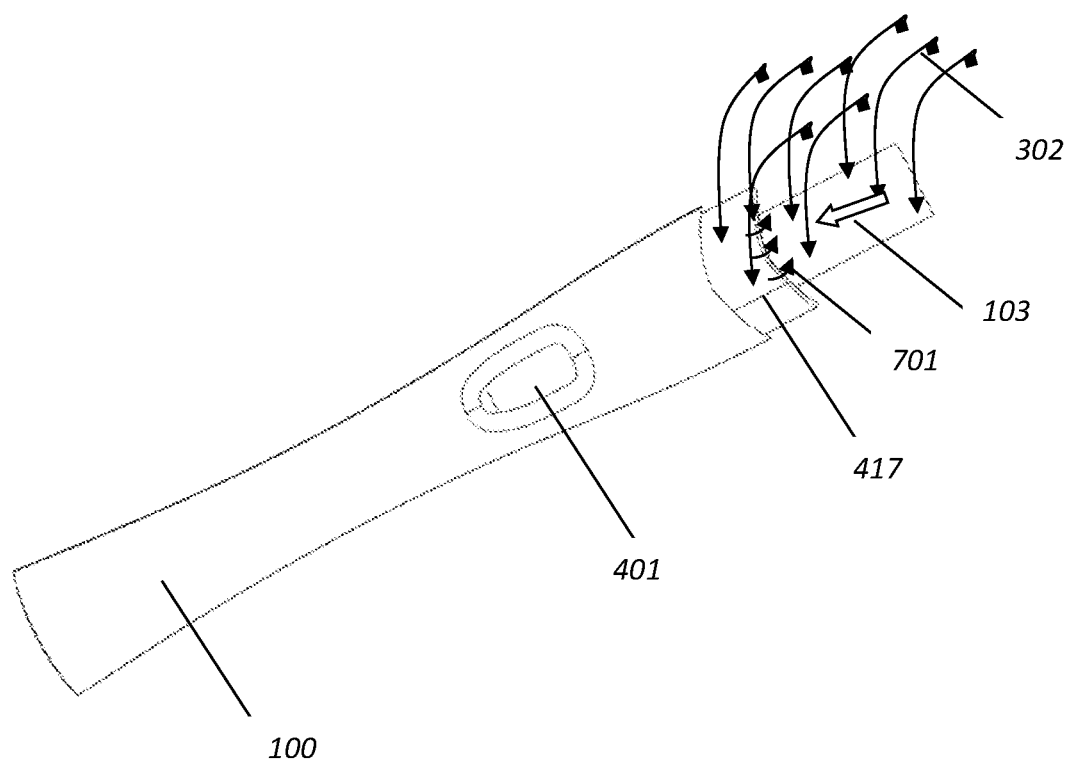
FIG. 10 is a schematic diagram showing an operation state of a test device for receiving a urine sample and a diversion element for receiving a urine sample according to another embodiment of the present invention.

In order to give the test results in a short time as soon as possible, liquid needs to flow on the testing element as soon as possible. Another solution is to increase the amount of liquid, which inevitably brings other negative effects. For example, it is desired that amount of liquid is relatively large. In a conventional test device, liquid diverted by the diversion element generally flows to a relatively long sample application pad 201 through a testing element, and then flows to a label area depending on the capillary action of the sample application pad, so that the amount of liquid can be controlled. However, this needs to take a long time. In the present invention, liquid can directly flow from the diversion element to the label pad, thus reducing the flowing time of the liquid through the sample application pad and allowing it to enter the label pad in advance. However, liquid from the diversion element has much larger volume and faster flow rate than liquid from a conventional sample application area, so that the amount of the liquid from the diversion element needs to be additionally controlled and negative adverse factors are reduced. The test device of the present invention is structurally improved, avoiding abnormal test results caused by the flooding phenomenon generated by excessive liquid. In addition, the liquid from the diversion element is blocked to gradually reduce its flow rate. Another problem is that at present, an early pregnancy test is performed by women themselves at home. When using the diversion element 10, women directly hold one end of the diversion element with their hands, for example, a position 100 as shown in FIGS. 9-10. Then, the other end 103 (exposed) of the diversion element 10 is used to receive a urine sample. Generally, the diversion element is placed under or near the urethra, and women urinate directly thereon for detection. Here, one end of the diversion element is located in the housing and directly connected with the label pad, and the other end thereof protrudes from the housing to receive the urine sample. For many domestic test devices, although operators have operation instructions, they usually don't read the instructions carefully. Even after reading the instructions, sometimes they still operate inappropriately. Further, for such test, it is desired that women urinate directly on the diversion element. Firstly, women hold the test device at different angles (FIGS. 9-10). For example, FIG. 9 shows that the test device is located directly below the urethra, and FIG. 10 shows that the test device is inclined and the diversion element is closer to the urethra. Secondly, as the amount of urine directly dripping onto the diversion element is relatively large, a test subject is difficult to control the amount when directly receiving the urine. In fact, when the test subject releases the urine in a normal condition, there is no special requirement for the amount of urine. Thirdly, the urinating duration of each person is different. From the above aspects, the amount of liquid is usually much larger than the required amount of liquid for detection. In addition, urine may directly come to the inlet 701 of the housing in terms of different operation angles, so that the urine directly enters the interior of the housing through the inlet. The inlet here is a mechanical gap between the housing and the diversion element. Generally, such gap is 1-2 mm and sometimes wider, so that urine directly enters the housing from the gap without passing through the diversion element, and may directly flow to the detection reagent strip at a relatively fast speed. In addition, the urine can directly drip onto a shoulder 417 and then flows black into the gap 701, and is gathered finally on the upper surface 108 of the diversion element 10.

Generally, the amount of urine is excessive. In this case, there is much liquid on the diversion element. A part of liquid 301 flows into the diversion element (as shown in FIG. 1) and then enters into the housing through the diversion element. The other part of liquid 302 can directly flow through the surfaces of the diversion element (upper surface 102, 108), directly enters into the housing (as shown in the schematic diagram of FIG. 1) and flows to the label pad 202. The flow rate of liquid flowing on the surface is fast due to the absence of resistance and faster than that of liquid flowing inside the diversion element, and the liquid flowing on the surface can reach the label area in advance. However, if too much liquid reaches the label area, the flooding phenomenon on the detection reagent strip is caused. In addition, liquid from the diversion element can flow from the liquid outlet end 104 of the diversion element to the label pad or from the place contacting the tail end of the diversion element to the label pad (FIGS. 2A-1B), as indicated by an arrow in FIG. 2B.

Figure 6:
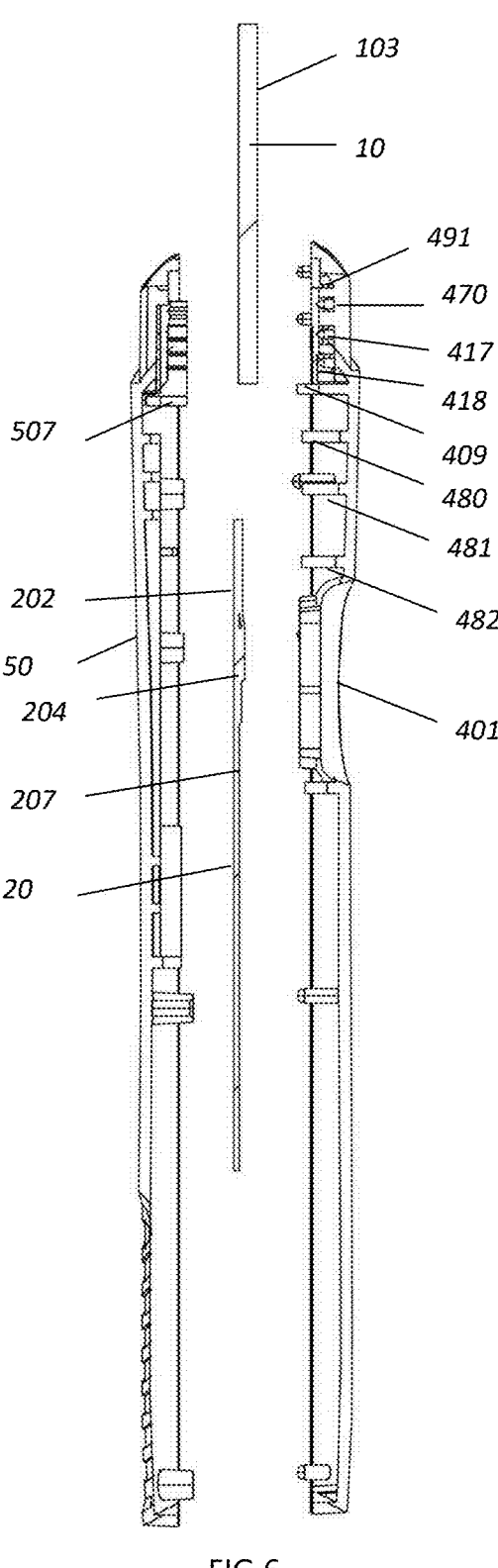
FIG. 6 is a schematic diagram showing a longitudinal cross-section structure of a test device in an assembly state according to an embodiment of the present invention.
Figure 7:
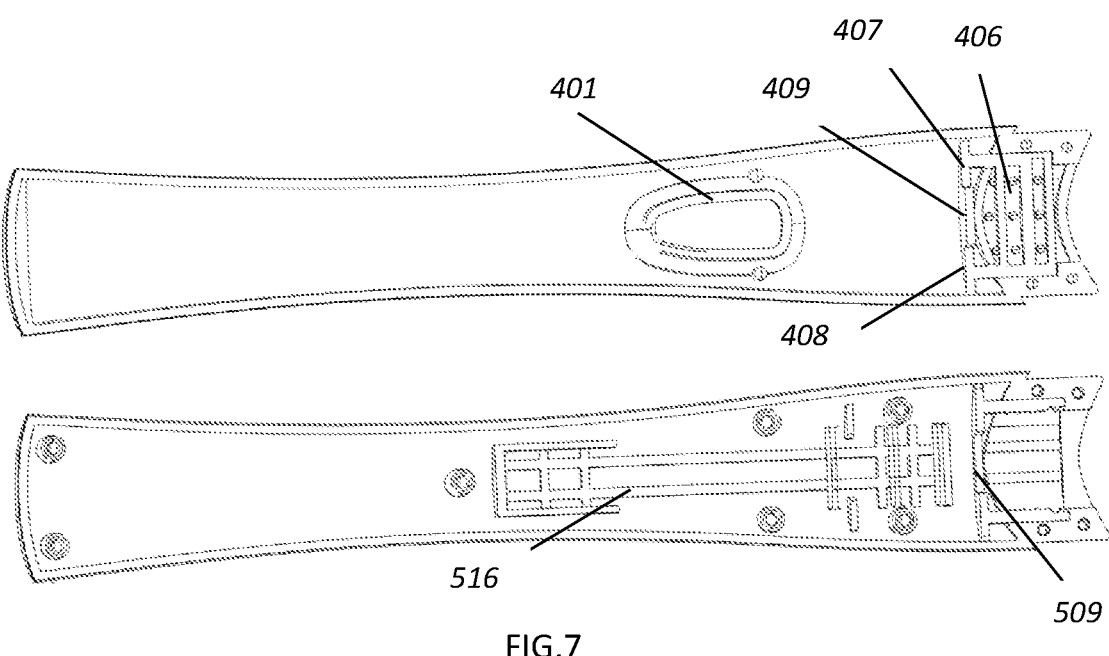
FIG. 7 is a schematic structural diagram of an upper housing and a lower housing according to an embodiment of the present invention.
Figure 8:
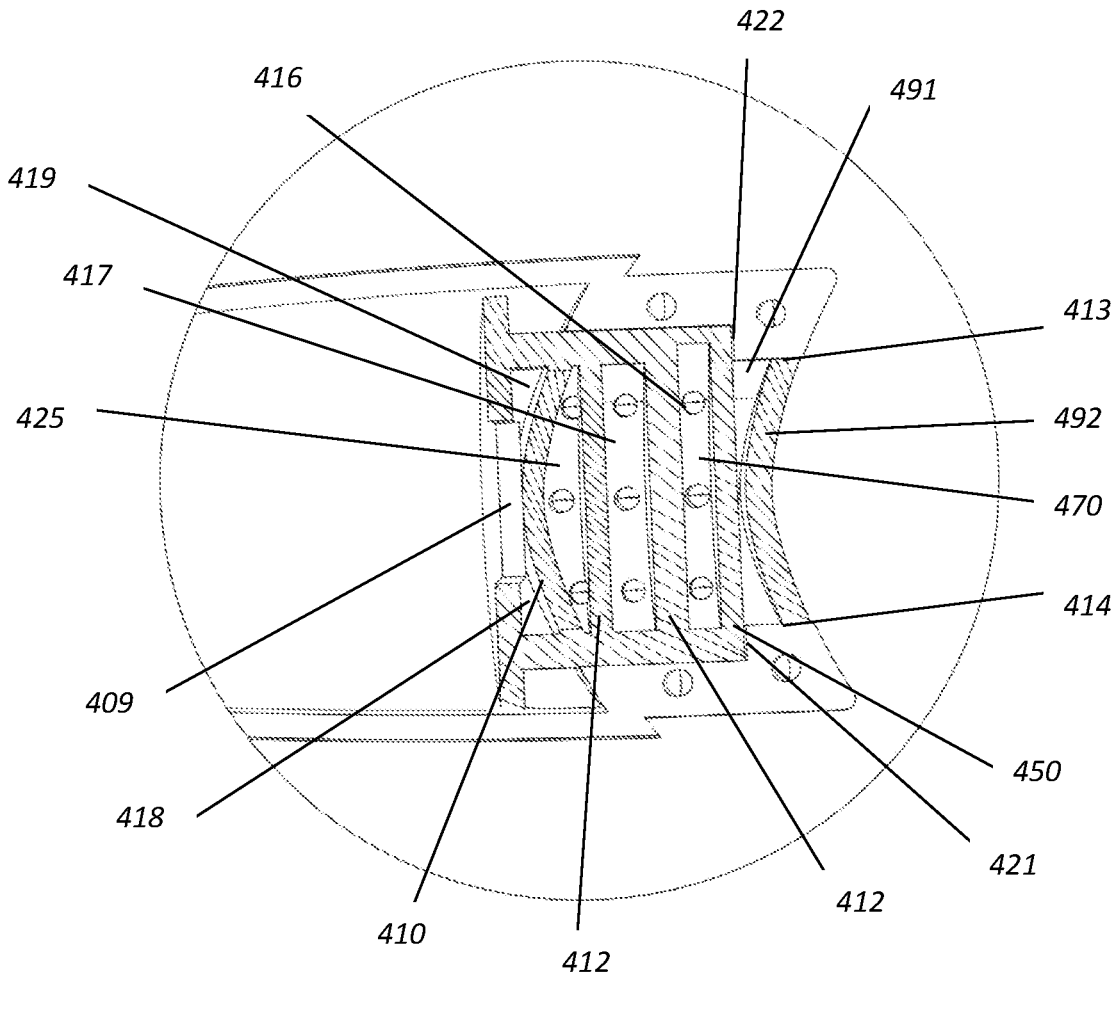
FIG. 8 is a schematic diagram showing an enlarged structure of a liquid retention chamber of an upper housing or an area where the liquid retention chamber is located according to an embodiment of the present invention.
Figure 11:
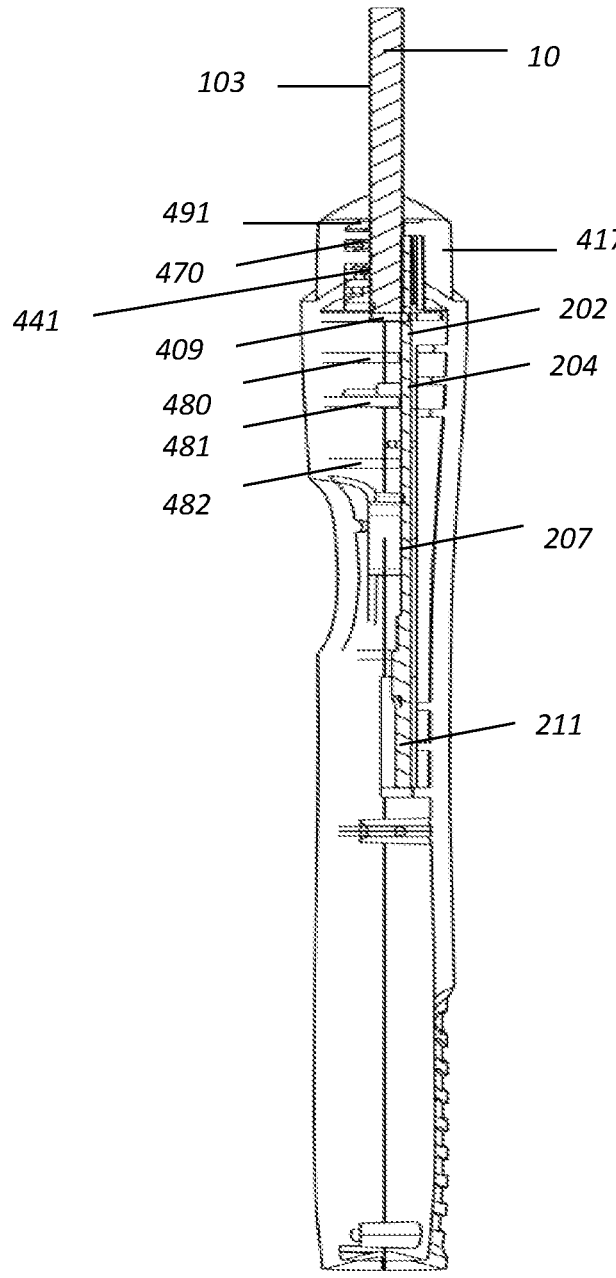
FIG. 11 is a schematic diagram showing a longitudinal cross-section structure of an assembled test device according to an embodiment of the present invention.
Figure 12:
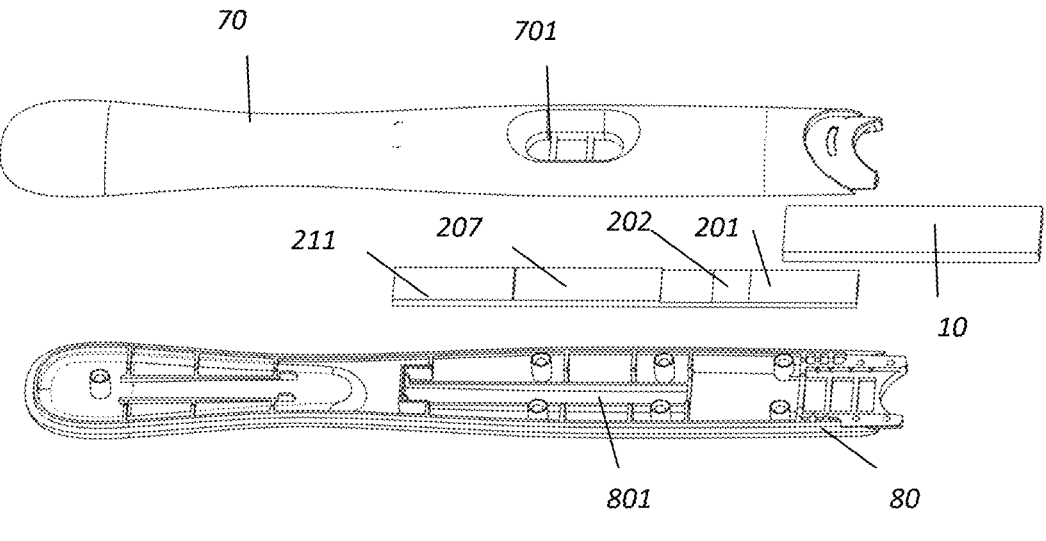
FIG. 12 is a schematic diagram showing an exploded three-dimensional structure of a test device according to another embodiment of the present invention.
Figure 13:
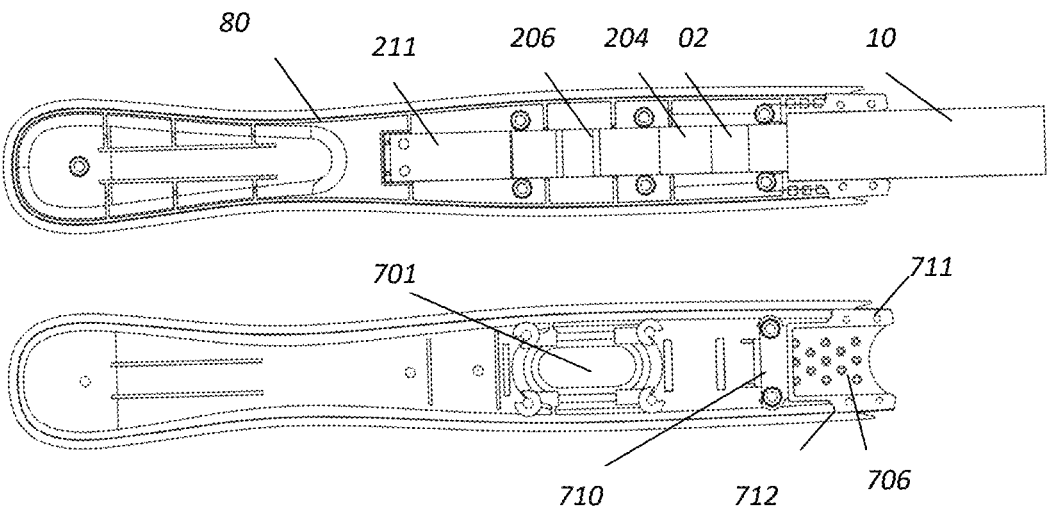
FIG. 13 is a schematic diagram showing an exploded three-dimensional structure of a lower housing including a testing element and an upper housing of a test device according to another embodiment of the present invention.
Figures 14, 15:
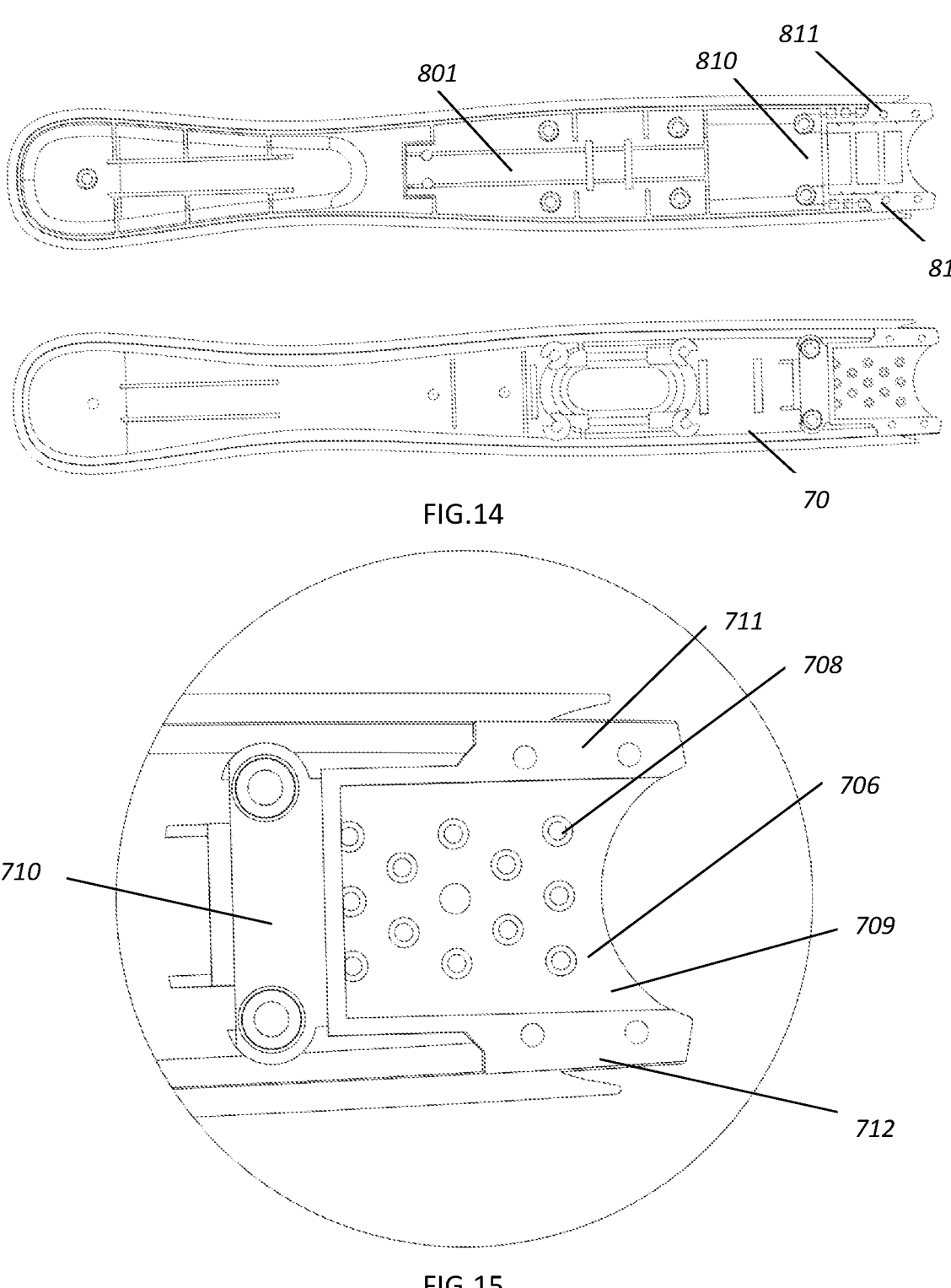
FIG. 14 is a schematic structural diagram of an upper housing and a lower housing according to another embodiment of the present invention.
FIG. 15 is a schematic diagram showing an enlarged structure of a liquid retention chamber of an upper housing according to an embodiment of the present invention.
Figure 16:
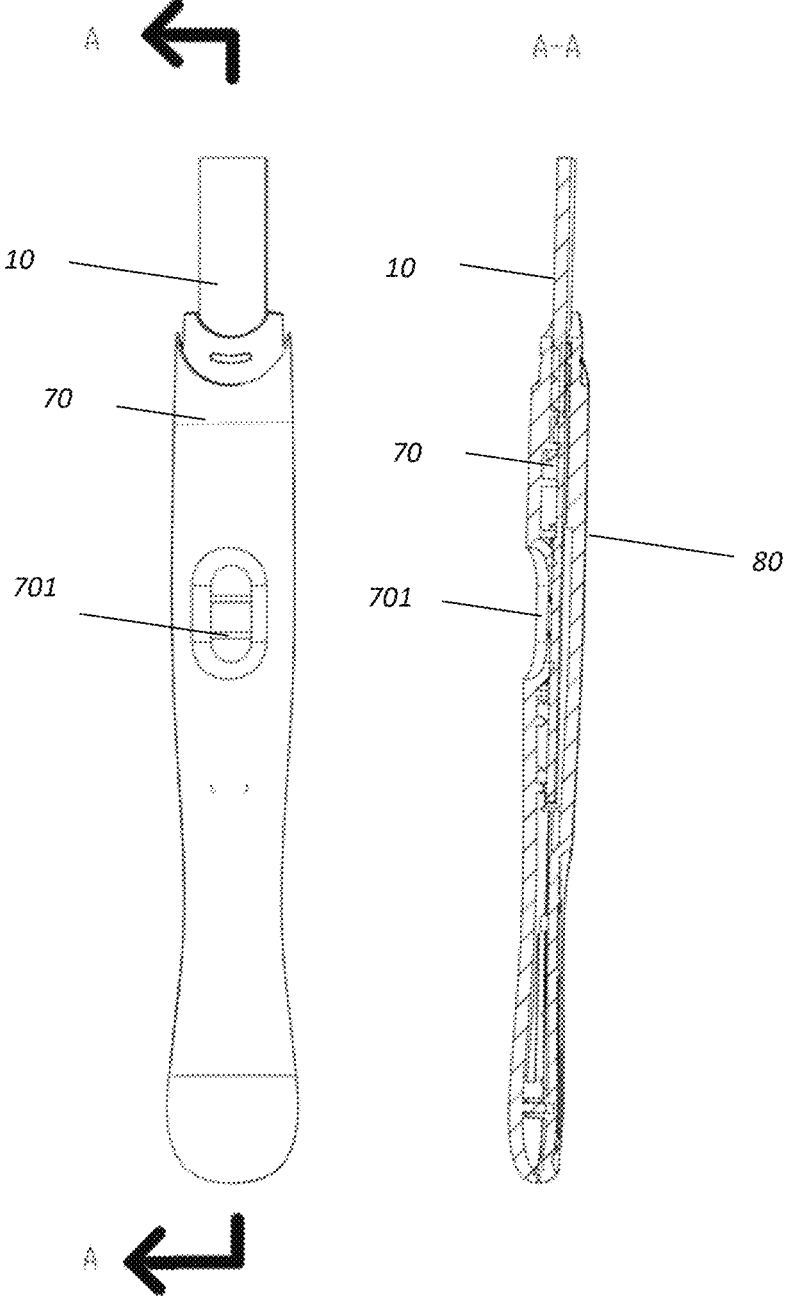
FIG. 16 is a top view of an assembled test device and a schematic diagram showing a cross-section structure thereof according to an embodiment of the present invention.

Therefore, in order to avoid negative impact on test results caused by the large amount and fast flow rate of liquid under different conditions of operators, the test device of the present invention is provided with spaces where excessive liquid can be accommodated when the liquid from the diversion element enters the housing, so that the excessive liquid can flow into the space, which reduces liquid from the surface of the diversion element to the detection reagent strip. The spaces retained are beyond the space where the detection reagent strips are located. If any detection reagent strips or a part of detection reagent strips are absent in these liquid retention chambers or spaces, retained liquid does not contact the detection reagent strips. As shown in FIGS. 4, 5 and 6, the liquid retention spaces are disposed on the upper housing (the detection reagent strip of the present invention is disposed on the lower housing instead of the upper housing), transverse grooves 491, 470, 417, 418 are formed in the upper housing through gullies between convex support strips 492, 450, 412, 451, 460. Specifically, there is a gap between the press strip 492 and the press strip 450, thereby forming the groove 491. As the press strip 492 is located at outermost and arched, the groove 491 has two parts. The groove 470 is formed between the press strip 450 and the press strip 412, the groove 417 is formed between the press strip 412 and the press strip 451, and the groove 418 is formed between the press strip 451 and the press strip 460. These grooves are perpendicular to the longitudinal direction of the diversion element, and the press strips all have flat surfaces. When the upper housing is combined with the lower housing, the flat surface is in contact with the upper surfaces 108 of the diversion element and the grooves with openings also cover the surfaces of the diversion element (as shown in FIGS. 6, 11 and 7). These press strips perpendicular to the diversion element (or arranged horizontally) cover the upper surfaces 108 of the diversion element 10. The press strips are to mainly slow down the flow rate of liquid on the diversion element, and the grooves formed by spacing the support strips and the press strips are used to accommodate excessive liquid which can enter the space partitioned by the press strips to be retained. The liquid does not move in the groove or the chamber due to the present of surface tension, and is difficult to flow due to limitation of the press strips. There may be one or more of the grooves or spaces, and the spaces cover the upper surface 108 of the diversion element. They are particularly useful for a case that urine directly drips into the gap 701 between the housing and the diversion element. The urine can be trapped by the liquid retention spaces, the liquid retention chambers, or the groove, thereby reducing liquid directly flowing to the label pad 202. In some embodiments, in order to enhance the fixation of the diversion element, a plurality of protruding pressing nails 416 are also disposed in the grooves and directly pressed into the surface of the diversion element, so that the diversion element is fixed and difficult to fall off from the housing, the liquid flow is also limited, and the flow of liquid entering into the groove is reduced due to the limitation of the pressing nails 416. After many clinical trials, the volume of the liquid retention space being controlled at 0.5-1 ml is enough to reduce excessive liquid flowing to the label area. Under such as volume, it is allowed to block a part of liquid from the surface of the diversion element using the press strips 492, 450, 412, 451, 460 one by one, and then excessive liquid is retained in the grooves. With the design of the above structure and the blocking of the pressing nails 416, the flow rate of liquid is slowed down, so that the liquid flows to the label pad and can contact substances on the label pad and moisten them.

Liquid passing through the interior of the diversion element can continuously flow to the label pad due to its slow flow rate, so that the amount of the liquid is appropriate and the liquid can fully moisten the labels and flow to the downstream of the testing area. If the liquid retention space cannot retain more liquid due to its small volume, liquid flows to the label pad. In case of excessive liquid, the flooding phenomenon is caused, which leads to invalid detection. If the liquid retention space is relatively large, a large housing space is needed. In addition, during many clinical tests of the diversion element, liquid collected is about 1-2 ml, liquid retained is 0.5-1 ml, and the liquid sample entering into the detection reagent strip is about 0.5-1 ml, which can achieve the flow of liquid on the detection reagent strip and the test.

In some embodiments, the upper housing further includes some grooves 415, 420 disposed near the longitudinal edge of the diversion element 10. It can be seen from FIG. 6 that the width of the diversion element is equal to the distance defined by two sides 413, 414 of the housing, the width of the longitudinal groove is the width of sides 422, 421, and the distance between the widest sides of the longitudinal grooves is greater than the width of the side defined by the diversion element. In this way, liquid from the edge of the diversion element is accommodated or retained by the longitudinal grooves. The areas where these transverse grooves and longitudinal grooves are located are lower than the edge areas as a whole, and the edge areas are provided with bolts 405, 404, 402, 403 fitting with sockets on the edge areas of the lower housing, so that the upper housing and the lower housing can be assembled together. In this way, excessive liquid on the diversion element is accommodated by these accommodating chambers, and the accommodating chambers retain the liquid through the capillary force or the surface tension of liquid. The transverse grooves, small gaps, and longitudinal grooves can be called capillary grooves or capillary spaces, and the capillary grooves can retain the liquid without easy flow. Of course, many capillary channels can be provided and also retain excessive liquid on the diversion element. However, the cost of providing the capillary channels on the housing is relatively high, so it is feasible to provide some non-capillary grooves, holes, and chambers to accommodate the excessive liquid.

The above is to reduce liquid on the surface of the diversion element flowing to the label area of the detection reagent strip, and the following is to reduce liquid from the diversion element flowing onto the label area of the detection reagent strip or slow down its flow rate.

Therefore, in some embodiments, a blocking plate 409 is disposed on the housing and used to block an end portion of the diversion element, thereby reducing liquid flowing to the label area. Typically, the blocking plate 409 is convex and located on the upper housing, and the diversion element 10 has a specified thickness as much as 2-3 times of the thickness of the testing element. As the diversion element has a large aperture, liquid quickly flows thereon. However, as the label pad has a compact texture and a small aperture, liquid slowly flows thereon. In this way, liquid directly flowing from the liquid outlet end 104 of the diversion element has an impact force on the label pad. Excessive liquid (if any) quickly flows directly from the surface of the label pad to the testing area to moisten it in advance, thereby causing the flooding phenomenon and affecting the testing accuracy. In order to avoid this problem, the lower housing 50 is further provided with the recess 509 by which the partition is divided into two parts, the blocking plate 409 is directly clamped at the recess to abut against the liquid outlet end 104 of the diversion element, for example, the blocking structure 900 as shown in FIG. 2 (FIG. 2 is a schematic structure). In this way, the end portion of the diversion element is abutted against the surface of the blocking plate 409. If excessive liquid flowing from the end portion of the diversion element is blocked by the blocking plate 409, it flows into the accommodating area of the lower housing 50, and a part of liquid flows into the chamber near the blocking plate 409, for example, the chamber of the upper housing and the grooves 418, 417. With the design of the structure, the liquid on the diversion element flows from its interior to the greatest extent, and then flows from the place where the liquid contacts the label pad to the label pad to the greatest extent (as indicated by an arrow in FIG. 2A). When the liquid flows the end portion, it is blocked to lower its flow rate, so that it can reach the label area smoothly, which avoids inaccurate test results caused by excessive liquid flowing to the detection reagent strip. This is because the end portion of the diversion element is directly connected with the label pad, and the distance between the end portion of the diversion element and the label area of the label pad is very close, and urine flowing from the end portion of the diversion element can directly flow to the label-containing area on the label pad. Therefore, the amount and flow rate of the liquid flowing from the end portion of the diversion element are also controlled.

In some embodiments, liquid directly flows from the diversion element to the label area, and the distance between the label area and the T line area of the testing area is relatively short. In order to improve the detection sensitivity, the liquid contacting the dry label on the label area is relatively given more time, and the analyte in the liquid reacts with the label. The upper housing is further provided with some blocking sheet structures having a specified thickness such as 1-2 mm. When these sheet structures are connected with the upper housing 40 and the lower housing, a first blocking press strip 480 is respectively applied to the overlapping position of the first label pad and the second label pad, and a second blocking press strip 481 is applied to the overlapping position of the second label pad and the testing pad (nitrocellulose membrane). With the blank area of the label pad being disposed at the recess 509, the blocking plate 409 locally exerts a specified pressure on the blank area of the label pad when blocking the end portion of the diversion element, and the liquid on the label pad flows from the upstream to the downstream where the blocking plate contacts the blank area, and the blocking plate 409 also has the function of delaying the flow rate. When there is the sample application pad 201, the blocking plate 409 is applied at the overlapping position of the sample application pad and the first label pad. These blocking plates disposed on the label pad are used to delay the flow of liquid and block excessive liquid, especially for liquid flowing rapidly from the surface of the label pad (which cannot carry enough labels or dissolve few labels), so that the testing area is as much as possible moistened by the label-containing or label-dissolved solution instead of being moistened in advance, improving the detection accuracy.

In other embodiments, for example, as shown in FIGS. 12-16, the testing element is disposed between the upper housing 70 and the lower housing 80. A window 701 for displaying the test results is disposed on the upper housing and corresponds to the testing area of the testing element. The testing element further includes a first label area 202 and a second label area 204, and a sample application area 201, where the sample application area is covered by the diversion element 10. One sample retention area 706 is disposed on the upper housing and a recessed outlet corresponding to the side 710 with respect to two sides 711, 712 and the side 710 covering the detection reagent strip. The entire recessed area is a liquid accommodating chamber. When the upper housing and the lower housing are assembled, two sides 711, 712 of the upper housing are combined with two sides 811, 812 of the lower housing through bolts and sockets, so the sides are in contact with each other and sealed. The diversion element is extruded between the side 810 of the lower housing and the side 710 of the upper housing through the bolts and the sockets, so that the liquid on the surface of the diversion element can be blocked through the sides 810, 710. However, excessive liquid is kept in the recessed area 706, to avoid it from entering the testing element 20. A plurality of small holes 708 are disposed in the recessed area 706 and can accommodate liquid. Of course, as the small holes have surface tension, the liquid therein is not easy to flow.

Example 1 Fabrication of Lateral Flow Test Device for Detecting HCG in Urine by Immunoassay Provided in the Present Invention As shown in FIGS. 3-11, a lateral flow test device for detecting HCG in urine by immunoassay according to this embodiment includes a detection reagent strip; from upstream to downstream according to the liquid flow direction, it sequentially includes a diversion element (a diversion pad 10 with a length of 40 mm, a thickness of 3 mm, and a width of 11 mm, made of macroporous fiber absorbent paper), a first label area (a first label pad), a second label area (a second label pad), and a testing area; the testing area and the control area are located on a nitrocellulose membrane, where the first label area and the second label area are made of a polyester film; the first label area is sprayed with a first HCG antibody marked with gold particles, and the second label area is sprayed with a second HCG antibody marked with latex particles; and the label pads both have blank areas without any labels. The liquid outlet end of the diversion element is spaced from the label-containing area of the first label area by 2 mm; the overlapping length thereof is 2 mm; the length of the diversion element is 40 mm and the width thereof is 11 mm; and the width of the label pad and the testing pad is 7 mm. The length of the first label pad with the label is 9 mm (the length of the label-containing area is 5 mm and the length of the blank area is 4 mm), the length of the second label pad with the label is 8 mm (the length of the label-containing area is 4 mm and the length of the blank area is 4 mm), and the tail end of the second label pad is spaced from the testing area (T line) by 7 mm.

The label area is made into the label pad and includes an antibody conjugated with label particles (for example, gold particles, latex particles or dyes, or other colored labels). Then, a label mixture is sprayed on the polyester film by spraying equipment to be made into the label pad; the label on the label pad can flow along with liquid; the nitrocellulose membrane is used in the testing area, the antibody or antigen of the test line is dissolved with a buffer solution PBS, and the nitrocellulose membrane is scribed by a film-spotting device and then dried in an oven for later use. The antibody treated on the membrane usually does not move.

The length of the diversion element in the housing is 13 mm, located under the groove channel in the housing (upper housing) and covered by the channel of the upper shell, covering the upper surface of the diversion element through the press strip. In addition, grooves (415, 420) with a width of 2 mm and a length of 11 mm are formed in both sides of the diversion element. These transverse grooves or bilateral grooves are also used to store excessive samples. In short, it is desired that liquid flowing onto the testing element is only the liquid flowing into the diversion element, and it is undesired that liquid beyond the diversion element flows onto the testing element. This is because too much liquid flowing to the testing element can cause flooding or inaccurate testing and false negative results. The term "into the diversion element" means that liquid flowing onto the diversion element flows into the diversion element. The term "beyond the diversion element" means that liquid is applied to the diversion element, and a part of liquid enters into the diversion element, while the part of liquid flows on the specific surface of the diversion element.

The diversion pads, first and second label pads, and testing pads are fabricated respectively, and then assembled according to the following method: overlapping the label-containing area of the first label pad (gold particles) on the blank area of the second label pad and directly overlapping the diversion element on the blank area of the first label pad. Therefore, the length of the label area constituted by the label pads is 15 mm, the length from the end of the diversion element to the T line is approximately 24 mm, and the label-containing area of the second label pad is lapped onto the nitrocellulose membrane. The upper housing and the lower housing are assembled together according to manners as shown in FIGS. 4-5 to form a final product, as shown in FIG. 9, where several press strips (such as two press strips) of the upper housing are respectively pressed against the overlapping position of the first label pad and the second label pad and the overlapping position of the second label pad and the nitrocellulose membrane; and the blocking plate 409 of the diversion element is abutted against the liquid outlet end 104 of the diversion element 10. Here, the sample application area or the sample application pad 201 is absent.

Standard samples are used for testing, which include 20 ug/L, 30 ug/L and 50 ug/L HCG (human chorionic gonadotropin), respectively. Here, if HCG is 20 ug/L, the test result is negative, the T line is absent, and the test result is valid in the presence of the C line. If HCG is 30 ug/L and 50 ug/L, the test result is positive, with the T line, the test results are valid only when all samples have C lines.

Example 2: different from Example 1, the testing element further includes the sample application pad 201 located below the diversion element, where the sample application pad is 15 mm long, with 12 mm of the sample application pad covered by the diversion element and 3 mm of the sample application pad covering the second label pad. The liquid outlet end 104 of the diversion element covers the sample application pad, but the distance between the end portion and the first label pad is 2 mm as in Example 1. In this way, a part of liquid from the diversion element flows to the label pad in advance, and a part of liquid from the diversion element flows from the sample application pad 201 to the label pad.

Example 3: no chamber is provided in the upper housing where the diversion element is located, such portion is a flat structure covering the surface of the diversion element, and the others are the same as those in Example 1.

Example 4: for the test device without the blocking plate 409, no blocking plate is used to block the end portion of the diversion element, and other structures are the same as those in Example 1.

Example 5: only one label pad is provided, its marked amount is the sum of two marked amounts in the example, gold particles and latex can be mixed and sprayed on one label pad, and the others are the same as those in Example 1.

Experimental process: in different experimental groups prepared, each 20 samples are respectively provided for devices in Examples 1-5, and then standard samples prepared are used for indoor test. The testing method is as follows: aspirate 50 ml sample with a pipettor, quickly apply it to the diversion element, simulate the action of female urination for testing, and observe the presence or absence of the T line and the C line in 2 minutes.

TABLE 1

| | Experimental results for 2 minutes | | |
| --- | --- | --- | --- |
| Example | 30 ug/L positive standard (positive result +/ negative result −) | 20 ug/L (negative result −/ invalid result) | 50 ug/L positive standard (positive result +/ negative result −/ invalid result) |
| Example 1 | 20+/0 | 20−/0 | 20+/0/0 |
| Example 2 | 19+/1− | 19−/1+ | 19+/1− |
| Example 3 | 15+/2−/3 invalid results | 19−/1 invalid result | 16+/2−/2 invalid results |
| Example 4 | 16+/2−/2 invalid results | 18−/2 invalid result | 17+/2−/1 invalid result |
| Example 5 | 14+/6−/0 | 20−/0 | 18+/3−/0 |

Note: the negative result of the positive samples here means absence of the T line and presence of the C line. An invalid result means absence of the C line.

At the time of 2 minutes, the test results in Example 1 have 20 positive results. This means that detection can be achieved in Example 1 when female urination is simulated in the laboratory, only there is one false negative. However, the positive detection rate in Example 2 has a slight decrease. This means that in the presence of the sample application pad, the positive detection rate relatively decreases with one false negative because there may be still more liquid. In Example 3, there is no structure for accommodating redundant samples on the diversion element. For 30 ug/L positive standards, there are 15 positive results, 2 false negative results, and 3 invalid results. This means that too much liquid flowing to the label area causes flooding, 2 standards are absent from the T line, other 3 standards are absent from the C line, and the label is not fully dissolved. Therefore, no line visible to the naked eye appears on the T line. In the absence of the blocking plate, the amount of liquid is also relatively large, with 4 wrong results (Example 4). In Example 5, there are only 14 positive results, meaning that the sensitivity is reduced. Compared with 50 ug/L positive standards, the positive detection rate in Example 5 is increased, but there are still three false negatives. This means that the detection sensitivity can be improved through two label pads. For negative samples, there are invalid results in Examples 3-4. For positive samples with high concentration, there are still invalid results and false negatives in Examples 3-4. This may be caused by too much liquid flowing from the surface of the label pad without fully dissolving the label.

The above five examples are used to conduct clinical trials, in which each 100 positive pregnant women having HCG above 50 ug/L are selected. They normally urinate on the diversion element according to the operating instructions. Results are read at 2 minutes and 5 minutes as follows:

| Example | Pregnant women (positive/negative) | Number of samples without C line displayed |
| --- | --- | --- |
| Example 1 | 99+/1 | 1 |
| Example 2 | 95+/2− | 3 |
| Example 3 | 75+/12− | 13 |
| Example 4 | 80+/10− | 10 |
| Example 5 | 90+/10− | 0 |

From the clinical trial, among positive women, the test device of the present invention can correctly detect that only one result is invalid. In Example 2, there are 3 invalid results, two of which are false negative results. In Examples 3-4, there are more invalid results, and the number of false negative results increases. This means that the amount of liquid is relatively large, and excessive urine flows from the detection reagent strip to the label area, and then quickly flows to the downstream without being fully dissolved on the label area, thereby resulting in false negative (no lines or invisible lines on the T line). As for Example 5, in a case that there is one label pad, 90 positive results and 10 negative results (false negatives) are obtained. In this example, when HCG in urine is equal to or less than 20 ug/L, it should be a negative result. Clinical results are all filled in by test subjects themselves, while laboratory results are determined by experimenters according to the operating instructions.

All the patents and publications mentioned in the description of the present invention indicate that these are public technologies in the art and can be used by the present invention. All the patents and publications cited herein are listed in the references, just as each publication is specifically referenced separately. The present invention described herein can be realized in the absence of any one element or multiple elements, one restriction or multiple restrictions, where the limitation is not specifically described here. For example, the terms "comprising", "essentially consisting of" and "consisting of" in each example herein may be replaced by the rest 2 terms. The so-called "a/an" herein merely means "one", but does not exclude including 2 or more instead of including only one. The terms and expressions which have been employed herein are descriptive rather than restrictive, and there is no intention to suggest that these terms and expressions in this description exclude any equivalents, but it is to be understood that any appropriate changes or modifications can be made within the scope of the present invention and appended claims. It can be understood that the examples described in the present invention are some preferred examples and features. A person skilled in the art can make some modifications and changes according to the essence of the description of the present invention. These modifications and changes are also considered to fall within the scope of the present invention and the scope limited by independent claims and dependent claims.

The invention claimed is:

1. A test device for detecting an analyte in a liquid sample, the test device comprising:

a label pad, containing a label;

a lateral flow testing element, having a nitrocellulose membrane in a testing area;

a housing, having an upper housing and a lower housing; and a diversion element, including a liquid outlet end;

wherein the label pad includes an end overlapping on the nitrocellulose membrane, the lateral flow testing element is located between the upper housing and the lower housing, the housing includes a housing end including a housing end opening, the diversion element includes a diversion element part located in the housing end opening, and the liquid outlet end of the diversion element is in contact with the label pad on the lateral flow testing element in the housing so that the liquid sample from the diversion element is capable of directly flowing to a label area;

wherein the lower housing includes a groove, the diversion element includes a diversion element surface, the lateral flow testing element is located in the groove, and the upper housing comprises a liquid retention chamber configured to receive a part of the liquid sample from the diversion element surface;

wherein the liquid retention chamber has a liquid retention chamber opening, the diversion element has a diversion element upper surface for receiving the liquid sample, and the liquid retention chamber opening is covered by the diversion element upper surface;

wherein the housing includes a housing inner surface, the liquid retention chamber is composed of compartment chambers formed by protruding plastic press strips set on the housing inner surface, and each of the press strips includes a press strip surface being in contact with the diversion element upper surface;

wherein the liquid outlet end includes a liquid outlet end portion, the test device further comprises a blocking element for reducing an amount and a flow rate of the liquid sample at the liquid outlet end portion flowing to the label area, wherein the blocking element is disposed in the housing, and the liquid outlet end portion is in contact with the blocking element.

2. The device according to claim 1, wherein the liquid retention chamber comprises one or more non-capillary grooves or non-capillary chambers.

3. The device according to claim 1, wherein the liquid retention chamber includes a liquid retention chamber end portion, the blocking element is disposed at the liquid retention chamber end portion, so as to reduce the amount and the flow rate of the liquid sample on the diversion element directly flowing to the label pad on the lateral flow testing element and to allow the liquid sample from the liquid outlet end to flow to the liquid retention chamber.

4. The device according to claim 3, wherein the blocking element is disposed on the upper housing, the lower housing is provided with a recess, the label pad includes a label pad part, the recess is provided with a blank area for disposing the label pad part, the diversion element includes a diversion element end portion, and the diversion element end portion is located on the blank area and in direct contact with the blank area.

5. The device according to claim 4, wherein when the upper housing and the lower housing are assembled together, the blocking element is inserted into the recess and in contact with the diversion element end portion.

6. The device according to claim 4, wherein the lateral flow testing element further comprises a sample application pad partially overlapped on the blank area on the label pad, the diversion element part covers the sample application pad, and the diversion element has an aperture or texture configured to allow the flow rate of the liquid sample on the diversion element to be greater than that of the liquid sample on the sample application pad.

7. The device according to claim 4, wherein the lateral flow testing element further comprises a sample application pad partially overlapped on the blank area on the label pad, and the diversion element part is overlapped on the sample application pad, wherein a part of the liquid sample from the diversion element flows into the sample application pad, and another part of the liquid sample from the diversion element directly flows to the label pad; and time when the liquid sample from the diversion element directly flows to the label pad is earlier than time when the liquid sample from the sample application pad flows to the label pad.

8. The device according to claim 5, wherein the label pad comprises a first label pad and a second label pad, wherein the first label pad is located upstream of the second label pad, and the liquid outlet end of the diversion element is overlapped on the first label pad.

9. The device according to claim 8, wherein the first label pad comprises a first label-free blank area and a first label-containing area, the second label pad comprises a second label-free blank area and a second label-containing area, and the diversion element end portion is overlapped on the first label-free blank area.

10. The device according to claim 9, wherein the nitrocellulose membrane comprises a test result area comprising a second antibody immobilized in the test result area and for specifically binding to the analyte, and each of the first label-containing area and the second label-containing area comprises a first antibody conjugated with latex particles or gold particles or both, and the first antibody is capable of specifically binding to the analyte.

11. The device according to claim 10, wherein the label pad composed of the first label pad and the second label pad has a label pad length, the label pad length is 15 mm, the liquid outlet end of the diversion element is spaced from the label area of the first label pad by 2 mm, and the second label pad is spaced from the testing area by 7 mm.

12. The device according to claim 11, wherein the second antibody specifically captures an HCG antigen, the first antibody specifically binds to the HCG antigen, and the liquid sample is a urine sample.

13. The device according to claim 12, wherein the label on the first label pad is the first antibody that is conjugated with gold particles and binds to HCG in urine, and the label on the second label pad is the first antibody that is conjugated with latex particles and specifically binds to HCG in urine.

14. The device according to claim 11, wherein the diversion element has a diversion element length, the diversion element length is 40 mm, the length of the diversion element located in the housing is 13 mm, the diversion element has a diversion element thickness, and the diversion element thickness is 3 mm.

15. The device according to claim 7, wherein the label pad comprises a first label pad and a second label pad, wherein the first label pad is located upstream of the second label pad, and the liquid outlet end of the diversion element is overlapped on the first label pad.

16. The device according to claim 15, wherein the first label pad comprises a first label-free blank area and a first label-containing area, the second label pad comprises a second label-free blank area and a second label-containing area, and the diversion element end portion is overlapped on the first label-free blank area.

* * * * *